(12) United States Patent
Hedrick et al.

(10) Patent No.: US 9,119,982 B2
(45) Date of Patent: Sep. 1, 2015

(54) FIRE EXTINGUISHING AGENTS, METHODS FOR PREVENTING AND/OR EXTINGUISHING COMBUSTION, FIRE EXTINGUISHING SYSTEMS, AND PRODUCTION PROCESSES

(75) Inventors: Vicki Hedrick, Brookston, IN (US);
John Chien, West Lafayette, IN (US);
Janet Boggs, Crawfordsville, IN (US);
Andrew Jackson, West Lafayette, IN (US); E. Bradley Edwards, Lafayette, IN (US); Stephan Brandstadter, Indianapolis, IN (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 13/405,710

(22) Filed: Feb. 27, 2012

(65) Prior Publication Data

US 2012/0175137 A1 Jul. 12, 2012

Related U.S. Application Data

(63) Continuation of application No. 11/559,330, filed on Nov. 13, 2009, now Pat. No. 8,148,584.

(60) Provisional application No. 60/735,717, filed on Nov. 10, 2005.

(51) Int. Cl.
| | | |
|---|---|---|
| A62D 1/00 | (2006.01) | |
| A62D 1/02 | (2006.01) | |
| C07C 17/25 | (2006.01) | |
| C07C 17/278 | (2006.01) | |
| C07C 21/18 | (2006.01) | |
| C09K 3/30 | (2006.01) | |
| C09K 21/08 | (2006.01) | |

(52) U.S. Cl.
CPC *A62D 1/00* (2013.01); *A62D 1/005* (2013.01); *A62D 1/0057* (2013.01); *A62D 1/0085* (2013.01); *C07C 17/25* (2013.01); *C07C 17/278* (2013.01); *C07C 21/18* (2013.01); *C09K 3/30* (2013.01); *C09K 21/08* (2013.01)

(58) Field of Classification Search
CPC ..... A62D 1/00; A62D 1/0057; A62D 1/0028; A62D 1/0092
USPC ............... 252/2, 3, 8; 570/123, 124
See application file for complete search history.

(56) References Cited

U.S. PATENT DOCUMENTS

| | | | |
|---|---|---|---|
| 3,723,318 A | 3/1973 | Butler | |
| 4,042,638 A | 8/1977 | Ozawa et al. | |
| 4,377,717 A | 3/1983 | Anello et al. | |
| 5,087,777 A | 2/1992 | Li et al. | |
| 5,205,956 A | 4/1993 | Volkert et al. | |
| 5,278,195 A | 1/1994 | Volkert et al. | |
| 5,300,534 A | 4/1994 | Volkert et al. | |
| 5,302,212 A | 4/1994 | Desbiendras et al. | |
| 5,741,825 A | 4/1998 | Inagaki et al. | |
| 5,993,682 A | 11/1999 | Tapscott et al. | |
| 6,065,547 A * | 5/2000 | Ellis et al. | 169/89 |
| 7,708,903 B2 | 5/2010 | Sievert et al. | |
| 2001/0032960 A1* | 10/2001 | Grzyll et al. | 252/2 |
| 2002/0002248 A1 | 1/2002 | Hung et al. | |
| 2004/0119047 A1 | 6/2004 | Singh et al. | |
| 2004/0256594 A1 | 12/2004 | Singh et al. | |
| 2007/0096051 A1 | 5/2007 | Nappa et al. | |

FOREIGN PATENT DOCUMENTS

| | | |
|---|---|---|
| DE | 4121161 A1 | 1/1993 |
| EP | 0520860 A1 | 6/1992 |
| EP | 0520860 B2 | 6/1992 |
| EP | 0520860 | 12/1992 |
| JP | 5179043 A | 7/1993 |
| WO | WO 97/07857 | 3/1997 |
| WO | US2006/060842 | 11/2006 |

OTHER PUBLICATIONS

Derwent Publications, XP002429063; RU 2071462 C1; Chem Techn; Jan. 1997; Abstract, 1 pg.
Derwent Publications, XP002429096; JP 05 042230 A; Daikin et al.; Feb. 1993; Abstract, 1 pg.
3M Novec™ 1230 Fire Protection Fluid, *Created for life*, Issued Sep. 2003, 6 pgs.
Kraft et al., *Mechanism of Vinylic and Allylic Carbon-Fluorine Bond* . . . , Journal of Am. Chem. Soc., vol. 124, No. 29, 2002, pp. 8681-8689.
Gauffreteau et al., *1-(Perfluoroisopropyl)-2-(perfluorohexyl)ethylene as a respiratory gas transport in intravascular usage*, Bulletin of Chem Soc. of France, Oct. 1984, pp. 562-567.
Petrov, *Direct synthesis of polyfluorinated allyl halides.* . . . , Journal of Fluorine Chem., 2002, pp. 23-26.

(Continued)

*Primary Examiner* — Khanh Tuan Nguyen
*Assistant Examiner* — Haidung Nguyen

(57) ABSTRACT

Compositions comprising

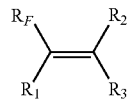

are provided wherein $R_F$ is a fluorine containing moiety comprising $(CF_3)_2CFCH_2(CF_3)CH—$, $(CF_3)_2CFCH_2((CF_3)_2CF)CH—$, $(CF_3)_2CFCH_2((CF_3)_2CH)CH—$, $(CF_3)_2CHCH_2((CF_3)_2CF)CH—$, $((CF_3)_2CFCH_2)_2CH—$, $(CF_3)_2CFCH_2CF—$, $(CF_3)_2CF—$, $(CF_3)_2CH—$, $CF_3—$, or $C_nF_{2n+1}—$, n being an integer from 2 to 20; $R_1$ is F or H; $R_2$ comprises $(CF_3)_2CF—$, $(CF_3)_2CH—$, $CF_3—$, F, or H; and $R_3$ comprises $(CF_3)_2CF—$, $(CF_3)_2CH—$, $CF_3—$, F, or H, such compositions can produced according to processes, and utilized to prevent combustion utilizing systems.

5 Claims, 2 Drawing Sheets

(56) References Cited

OTHER PUBLICATIONS

Chambers et al., *Reactions of novel unsaturated cluorocarbons*, Journal of Fluorine Chem., 2002, pp. 239-246.
Apsey et al., *Fluoro-alkene forming eliminations using antimony pentafluoride*, Journal of Fluorine Chem., 2002, pp. 127-132.
Fleming et al., *Addition of Free Radicals to Unsaturated Systems*, Journal of the Chem. Soc., 1973, pp. 574-577.
Perfluoro isopropyl etheylene chemical structure, Nov. 1984.
Journal Fluorine Chemistry, "Model Compoiunds Related to Hexafluoropropene-vinylidene Fluoride Elastomer", Apsey et al., 1988, 40 (2-3), pp. 261-282, Elsevier Sequoia, The Netherlands.
Tetrahedron, 1964, "Telomerization Reactions in the Synthesis of Models for Some Fluorocarbons Polymers" Chambers et al., vol. 20, pp. 497-506, Pergamon Press Ltd., Northern Ireland.
International Search Report, PCT/US2006/060842, Filed Nov. 13, 2006, Dalkafouki, A.

* cited by examiner

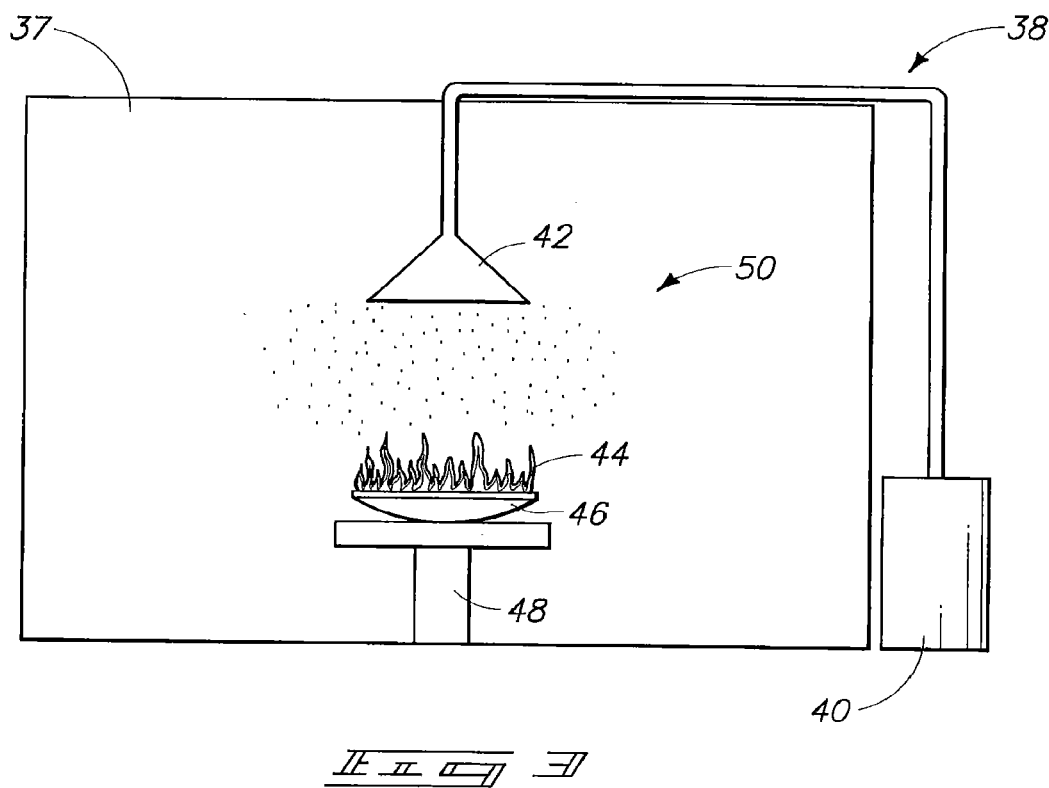

FIRE EXTINGUISHING AGENTS, METHODS FOR PREVENTING AND/OR EXTINGUISHING COMBUSTION, FIRE EXTINGUISHING SYSTEMS, AND PRODUCTION PROCESSES

CLAIM FOR PRIORITY

This application claims priority to U.S. Provisional Patent Application Ser. No. 60/735,717 entitled "Fire Extinguishing Agents, Methods for Preventing and/or Extinguishing Combustion, Fire Extinguishing Systems, and Production Process", filed Nov. 10, 2005, the entirety of which is incorporated by reference herein.

TECHNICAL FIELD

The present disclosure is directed to fire extinguishing agents and systems and methods of extinguishing and/or preventing combustion, as well as, production processes. In particular aspects, $R_F$-olefin compounds are described for use in fire extinguishing and/or preventing systems. Other aspects of the present disclosure are also directed to the production of these compounds.

BACKGROUND OF THE DISCLOSURE

Certain bromine, chlorine, and iodine containing halogenated chemical agents have been used to extinguish fires. The use of iodine-containing compounds as fire extinguishing agents has been avoided primarily due to the expense of their manufacture or due to possible toxicity considerations.

Bromine-containing and chlorine-containing compounds; Halon 251 ($CF_3CF_2Cl$) Halon 1301 ($CF_3Br$), Halon 1211 ($CF_2BrCl$), and Halon 2402 ($BrCF_2CF_2Br$) have been utilized to extinguish fires, for example. Although the above-named bromine or chlorine-containing Halons have been used, these agents have been asserted by some to be capable of the destruction of the earth's protective ozone layer. Also, because the agents contain no hydrogen atoms which would permit their destruction in the troposphere, the agents may also contribute to global warming.

More recently, hydrofluorocarbons have been proposed for fire suppression. However, a disadvantage of these compounds is their relatively high global warming potential.

The present disclosure provides novel compounds, combustion prevention compositions and systems, as well as, methods for using the same to extinguish and/or prevent combustion.

SUMMARY OF THE DISCLOSURE

A composition comprising

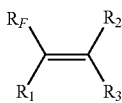

wherein $R_F$ is a fluorine containing moiety comprising $(CF_3)_2CFCH_2(CF_3)CH—$, $(CF_3)_2CFCH_2((CF_3)_2CF)CH—$, $(CF_3)_2CFCH_2((CF_3)_2CH)CH—$, $(CF_3)_2CHCH_2((CF_3)_2CF)CH—$, $((CF_3)_2CFCH_2)_2CH—$, $(CF_3)_2CFCH_2CF—$, $(CF_3)_2CF—$, $(CF_3)_2CH—$, $CF_3—$, or $C_nF_{2n+1}—$, n being an integer from 2 to 20; $R_1$ is F or H; $R_2$ comprises $(CF_3)_2CF—$, $(CF_3)_2CH—$, $CF_3—$, F, or H; and $R_3$ comprises $(CF_3)_2CF—$, $(CF_3)_2CH—$, $CF_3—$, F, or H.

A combustion prevention composition comprising

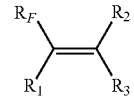

wherein $R_F$ is a fluorine containing moiety comprising $(CF_3)_2CFCH_2(CF_3)CH—$, $(CF_3)_2CFCH_2((CF_3)_2CF)CH—$, $(CF_3)_2CFCH_2((CF_3)_2CH)CH—$, $(CF_3)_2CHCH_2((CF_3)_2CF)CH—$, $((CF_3)_2CFCH_2)_2CH—$, $(CF_3)_2CFCH_2CF—$, $(CF_3)_2CF—$, $(CF_3)_2CH—$, $CF_3—$, or $C_nF_{2n+1}—$, n being an integer from 2 to 20; $R_1$ is F or H; $R_2$ comprises $(CF_3)_2CF—$, $(CF_3)_2CH—$, $CF_3—$, F, or H; and $R_3$ comprises $(CF_3)_2CF—$, $(CF_3)_2CH—$, $CF_3—$, F, or H.

A combustion prevention composition comprising $R_F—CR_1=CR_2R_3$, wherein the $R_F$ portion is $C_3F_7$ or $C_3F_6$, and the $R_1$, $R_2$, and $R_3$ portions are one or more of H, F, $CF_3$, and $C_3F_7$.

A production process comprising exposing an $R_F$-reactant to an olefinic reactant within a reaction vessel, the exposing producing and $R_F$-intermediate, wherein the $R_F$-reactant comprises at least three $—CF_3$ groups and the $R_F$-intermediate is a saturated compound comprising the three $—CF_3$ groups.

A production process comprising exposing an $R_F$-reactant to an olefinic reactant within a reaction vessel, the exposing producing and $R_F$-intermediate, wherein the $R_F$-reactant comprises at least one $(CF_3)_2CH—$ group and the $R_F$-intermediate is a saturated compound comprising the $(CF_3)_2CH—$ group.

A production process comprising exposing an $R_F$-reactant to an olefinic reactant within a reaction vessel, the exposing producing and $R_F$-intermediate, wherein the $R_F$-reactant comprises at least one $—CF_3$ group, the olefinic reactant comprises at least two $—CF_3$ groups, and the $R_F$-intermediate is a saturated compound comprising the one $—CF_3$ group of the $R_F$-reactant and the two $—CF_3$ groups of the olefinic reactant.

A combustion prevention process comprising providing a container housing a combustion prevention composition, the container being configured to couple to a combustion prevention composition distribution apparatus, the prevention composition comprising

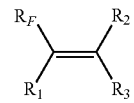

wherein $R_F$ is a fluorine containing moiety comprising $(CF_3)_2CFCH_2(CF_3)CH—$, $(CF_3)_2CFCH_2((CF_3)_2CF)CH—$, $(CF_3)_2CFCH_2((CF_3)_2CH)CH—$, $(CF_3)_2CHCH_2((CF_3)_2CF)CH—$, $((CF_3)_2CFCH_2)_2CH—$, $(CF_3)_2CFCH_2CF—$, $(CF_3)_2CF—$, $(CF_3)_2CH—$, $CF_3—$, or $C_nF_{2n+1}—$, n being an integer from 2 to 20, $R_1$ is F or H, $R_2$ comprises $(CF_3)_2CF—$, $(CF_3)_2CH—$, $CF_3—$, F, or H; and $R_3$ comprises $(CF_3)_2CF—$, $(CF_3)_2CH—$, $CF_3—$, F, or H.

A combustion prevention system comprising a container housing a combustion prevention composition, the combustion prevention composition comprising

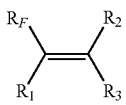

wherein $R_F$ is a fluorine containing moiety comprising $(CF_3)_2$CFCH$_2$(CF$_3$)CH—, $(CF_3)_2$CFCH$_2$((CF$_3$)$_2$CF)CH—, $(CF_3)_2$CFCH$_2$((CF$_3$)$_2$CH)CH—, $(CF_3)_2$CHCH$_2$((CF$_3$)$_2$CF)CH—, ((CF$_3$)$_2$CFCH$_2$)$_2$CH—, $(CF_3)_2$CFCH$_2$CF—, $(CF_3)_2$CF—, $(CF_3)_2$CH—, CF$_3$—, or C$_n$F$_{2n+1}$, n being an integer from 2 to 20, $R_1$ is F or H, $R_2$ comprises $(CF_3)_2$CF—, $(CF_3)_2$CH—, CF$_3$—, F, or H; and $R_3$ comprises $(CF_3)_2$CF—, $(CF_3)_2$CH—, CF$_3$—, F, or H; and a composition distribution apparatus coupled to the container, the apparatus configured to distribute the combustion prevention composition.

BRIEF DESCRIPTION OF THE DRAWINGS

FIG. 3 is an illustration of an application of combustion prevention compositions in accordance with an aspect of the present disclosure.

DETAILED DESCRIPTION OF THE DISCLOSURE

Figure 1:
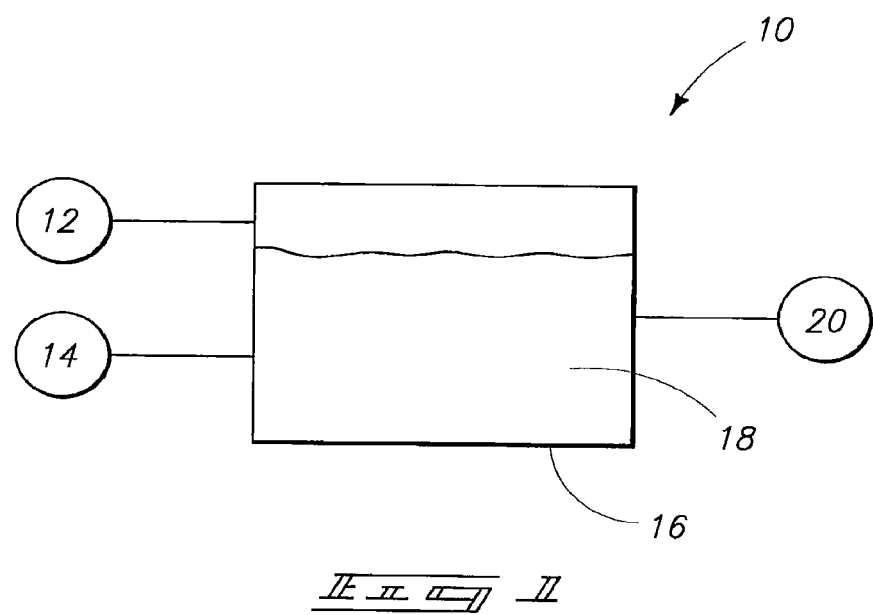
FIG. 1 is a diagram of one embodiment of halogenated intermediate production in accordance with an aspect of the present disclosure.

Fire extinguishing compositions and methods, as well as, materials and methods for producing the same are described with reference to FIGS. 1-3. Referring to FIG. 1, a system 10 is depicted that includes a $R_F$-reactant reservoir 12 and an olefinic-reactant reservoir 14 coupled to a reaction vessel 16. System 10 can be configured with these reaction reservoirs to produce a halogenated intermediate within halogenated intermediate reservoir 20.

Reaction vessel 16 can be configured as a commercially operable reaction vessel. Such reaction vessels include those reaction vessels configured to react compounds in the liquid phase and/or in the gas phase at predetermined pressures and/or temperatures. Reaction vessel 16 can include conduits for receiving reactants from reservoirs 12 and 14, as well as, conduits for providing product to reservoir 20.

The $R_F$-reactant can include halogenated and hydrohalogenated compounds such as $R_F$X. The $R_F$— can include a moiety such as $(CF_3)_2$CFCH$_2$(CF$_3$)CH, $(CF_3)_2$CFCH$_2$((CF$_3$)$_2$CF)CH, $(CF_3)_2$CFCH$_2$((CF$_3$)$_2$CH)CH, $(CF_3)_2$CHCH$_2$((CF$_3$)$_2$CF)CH, ((CF$_3$)$_2$CFCH$_2$)$_2$CH, $(CF_3)_2$CFCH$_2$CF, $(CF_3)_2$CF—, $(CF_3)_2$CH— or CF$_3$, and/or C$_n$F$_{2n+1}$, for example. The $R_F$— moiety can be bonded to a halogen X, such as F, Cl, Br, and/or I. The C$_n$F$_{2n+1}$ can have from 2-20 carbons. More particular examples of the $R_F$-reactant can include $(CF_3)_2$CFI, $(CF_3)_2$CFBr, $(CF_3)_2$CHBr, and/or $(CF_3)_2$CHI.

The $R_F$-reactant can include at least three —CF$_3$ groups, such as

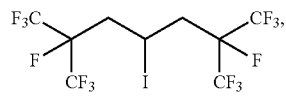

for example. The $R_F$-reactant comprises at least one $(CF_3)_2$CH— group, such as

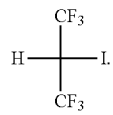

The $R_F$-reactant can be $(CF_3)_2$CH—X, with X being one or more elements of the periodic table of elements. According to exemplary embodiments X is a halogen or can comprise at least one halogen.

The $R_F$-reactant of reservoir 12 can be provided to reaction vessel 16 through a conduit using a pressure differential, for example, drawn under vacuum or forced under pressure. The $R_F$-reactant can also be provided alone or in combination with the olefinic-reactant of reservoir 14.

The olefinic-reactant can include ethylene and/or propene compounds such as C-2 and C-3 olefins. These compounds can include hydrofluorinated and/or hydrohalogenated compounds as well as perhalogenated and perfluorinated compounds. The olefinic reactant comprises at least one fluorine. The olefinic reactant can include one or more of —CF$_2$ or —CF$_3$ groups. The olefinic reactant can include at least two —CF$_3$ groups, such as

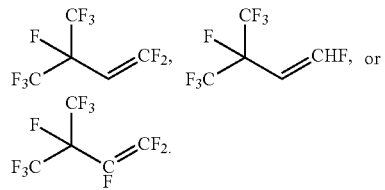

Exemplary olefinic reactants include, but are not limited to, ethylene, 3,4,4,4-tetrafluoro-3-(trifluoromethyl)but-1-ene, 4,4,4-trifluoro-3-(trifluoromethyl)but-1-ene, 3,3,3-trifluoroprop-1-ene, 1,1-difluoroethylene, fluoroethylene and/or perfluoroethylene. These reactants can be combined in reaction vessel 16 at a predetermined temperature in the presence of a media that can include methylene chloride and/or an aqueous solution of sodium metabisulfite from 20 to 40 (wt/wt) % to form a mixture 18.

According to another embodiment, the olefinic and $R_F$-reactants can be combined in the gas phase in the presence of substrate such as a catalyst, for example. Such gas phase reactions can include configuring vessel 16 as an Inconel® (INCO Limited Toronto, Canada) tube, such as OD=0.5", Length 14.125", wall thickness=0.035" tube packed with support. The support can include activated carbon and/or catalysts such as FeCl$_3$, NiCl$_2$, CuCl$_2$, and/or ZnCl$_2$. The system can be configured to vaporize the reactants prior to the reactants entering vessel 16. Products recovered from vessel 16 can be passed through a scrubbing apparatus, then dried using an apparatus such as a Drierite® (W.A. Hammond Drierite Co. Ltd. P.O Box 460 Xenia, Ohio 45385) tube and liquefied in a dry ice/acetone trap, for example.

In addition to mixture 18, a catalyst such as a free radical initiator and/or a metal salt can be added. Such exemplary free radical initiators can include benzoyl peroxide, azobisisobutyronitrile, and/or tert-butylperoxide. Such exemplary metal salts can include salts of copper, iron, zinc, silver, and mixtures thereof. In other examples, mixture 18 can be heated in the absence of a catalyst. The $R_F$-reactant can be exposed to the olefinic reactant in the presence of a catalyst. The catalyst can include one or more of benzoyl peroxide, azobisisobutyronitrile, and/or tert-butylperoxide, for example. Typically, the mixture and catalyst can be stirred and a halogenated intermediate can be formed and separated from the mixture.

The halogenated intermediate can include, but is not limited to, $R_F(R_2)_2C—C(R_1)_2X$. The $R_F$ moiety can be as previously described and $R_1$ and $R_2$ can be the same or different and can include hydrogen and/or fluorine, as well as, other halogenated moieties such as $CF_3$, for example. As described previously, X can be halogens such as I, Br and/or Cl. In accordance with at least some embodiments, the $R_F$-intermediate can be a saturated compound comprising three —$CF_3$ groups, such as

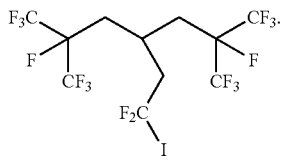

The $R_F$-intermediate can be a saturated compound comprising at least one $(CF_3)_2CH—$ group such as

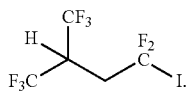

The $R_F$-intermediate can also be a saturated compound including the one —$CF_3$ group of the $R_F$-reactant and the two —$CF_3$ groups of the olefinic reactant, such as

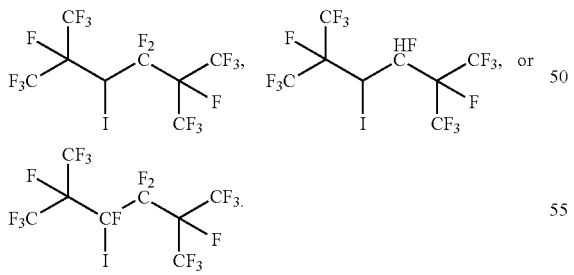

Exemplary conduits coupled to reservoir 20 include those conduits that can be coupled to separation devises such as a distillation apparatus. These separation devices can be configured to separate the halogenated intermediate from mixture 18.

Exemplary halogenated intermediates include those listed in Table 1 below.

TABLE 1

Exemplary Halogenated Intermediates

TABLE 1-continued

Exemplary Halogenated Intermediates (structures shown)

Figure 2:
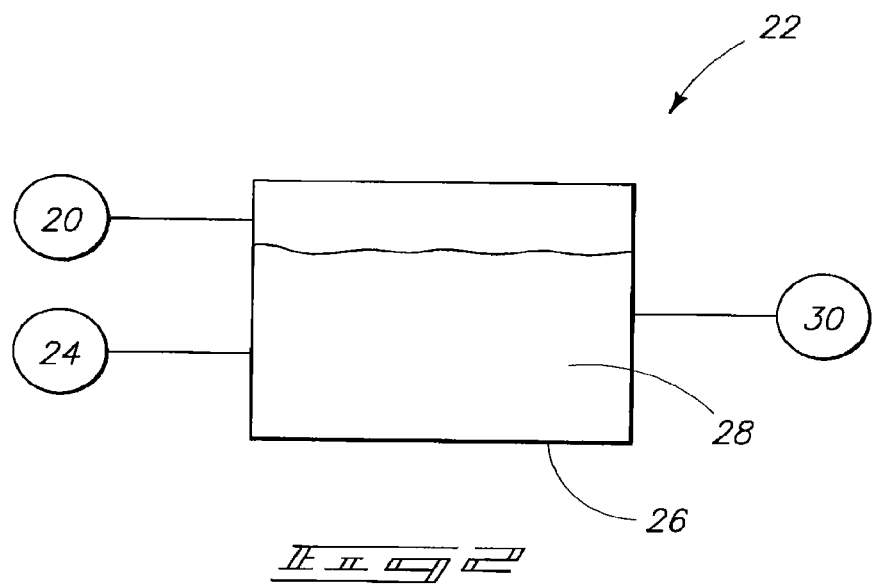
FIG. 2 is a diagram of one embodiment of $R_F$-olefin product production in accordance with an aspect of the present disclosure

Referring to FIG. 2, exemplary system 22 is depicted and includes a halogenated intermediate reservoir 20 and an elimination reactant reservoir 24 coupled to a reaction vessel 26. Reaction vessel 26 can be an industrial reactor configured to react organic compounds under predetermined temperatures and pressures. The reactor can be configured to include an agitating apparatus such as a mechanical stirrer. System 22 also includes an $R_F$-olefin product reservoir 30. Reservoirs 20, 24, and 30 can be coupled to vessel 26 via conduits configured to convey the halogenated intermediate, elimination reactant, and $R_F$-olefin product respectively. System 22 may be coupled to system 10 of FIG. 1.

According to exemplary embodiments, the halogenated intermediate of halogenated intermediate reservoir 20 can be combined with a media, such as methylene chloride and a phase transfer catalyst, such as a 75 percent (wt/wt) solution of methyltributylammonium chloride in water to form a mixture 28 within reaction vessel 26. The halogenated intermediates can include those halogenated intermediates described as well as listed above in Table 1, for example.

Upon forming mixture 28 within vessel 26, elimination reactant from elimination reactant reservoir 24 can be added to mixture 28. Exemplary elimination reactants include, but are not limited to 2,3,4,6,7,8,9,10-octahydropyrimido[1,2-a]azepine (DBU) and other dehydrohalogenating and/or dehalogenating reagents. Other exemplary eliminating reactants include mixtures of potassium hydroxide and water or alcohols such as methanol, and mixtures having a pH greater than 7. Additional elimination reactants that may be utilized are those reactants that can be utilized to remove a halogen selective to fluorines of a compound to form an olefin of the prior intermediate.

The $R_F$-olefin product can include, but is not limited to, the compound having the general formula $R_F(R_2)C\!=\!C(R_3)_2$. The $R_F$ moiety can be as previously described and the $R_2$ is as previously described. The $R_3$ moiety can either be the same or different and can include one or more of $(CF_3)_2CF$, $(CF_3)_2CH$, $CF_3$, F, and/or H. In more preferred embodiments, the $R_F$-olefin product can have a $R_3$ moiety that is the same as the $R_2$ moiety. The $R_F$-olefin product can be used as a fire extinguishing agent. Dimers of $R_F$-olefins can also be produced. For example, the $R_F$-olefin perfluoroprop-1-ene may be dimerized over carbon at elevated temperatures to form 1,1,1,2,3,4,5,5,5-nonafluoro-4-(trifluoromethlyl)pent-2-ene.

According to least some embodiments, the $R_F$-olefin product is

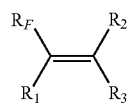

with $R_F$ being a fluorine containing moiety including $(CF_3)_2$ $CFCH_2(CF_3)CH\!-\!$, $(CF_3)_2CFCH_2((CF_3)_2CF)CH\!-\!$, $(CF_3)_2$ $CFCH_2((CF_3)_2CH)CH\!-\!$, $(CF_3)_2CHCH_2((CF_3)_2CF)CH\!-\!$, $((CF_3)_2CFCH_2)_2CH\!-\!$, $(CF_3)_2CFCH_2CF\!-\!$, $(CF_3)_2CF\!-\!$, $(CF_3)_2CH\!-\!$, $CF_3\!-\!$, or $C_nF_{2n+1}\!-\!$, n being an integer from 2 to 20; $R_1$ being F or H; $R_2$ including $(CF_3)_2CF\!-\!$, $(CF_3)_2$ $CH\!-\!$, $CF_3\!-\!$, F, or H; and $R_3$ including $(CF_3)_2CF\!-\!$, $(CF_3)_2$ $CH\!-\!$, $CF_3\!-\!$, F, or H. The compound

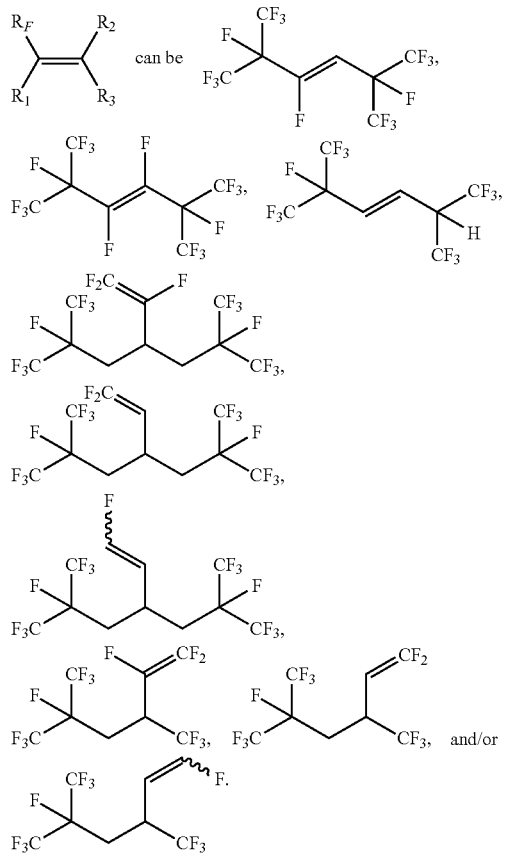

The $R_F$-olefin product is

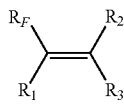

with $R_F$ being a fluorine containing moiety comprising $(CF_3)_2CFCH_2(CF_3)CH-$, $(CF_3)_2CFCH_2((CF_3)_2CF)CH-$, $(CF_3)_2CFCH_2((CF_3)_2CH)CH-$, $(CF_3)_2CHCH_2((CF_3)_2CF)CH-$, $((CF_3)_2CFCH_2)_2CH-$, $(CF_3)_2CFCH_2CF-$, $(CF_3)_2CF-$, $(CF_3)_2CH-$, $CF_3-$, or $C_nF_{2n+1}-$, n being an integer from 2 to 20, $R_1$ being F or H, $R_2$ being $(CF_3)_2CF-$, $(CF_3)_2CH-$, $CF_3-$, F, or H, and $R_3$ being $(CF_3)_2CF-$, $(CF_3)_2CH-$, $CF_3-$, F, or H. The compound

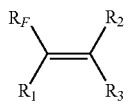

can be

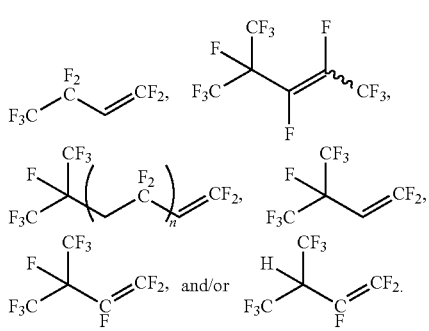

Exemplary $R_F$-olefin products are those shown in Table 2 below.

The following examples are exemplary of process conditions for producing halogenated intermediates and R$_F$-olefin products.

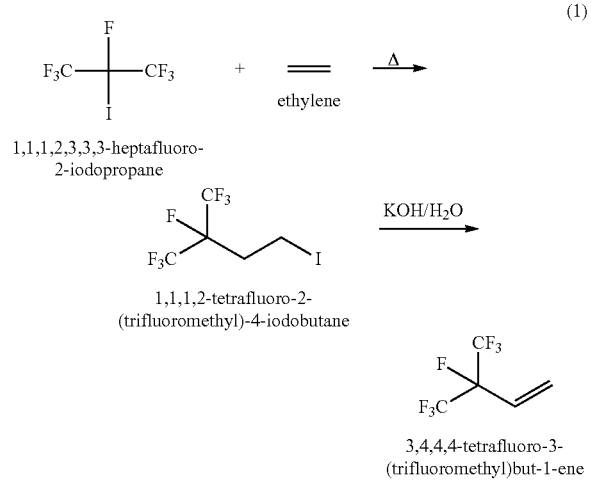

In accordance with scheme (1), in a 300 cc autoclave that can be equipped with mechanical stirring, rupture disc, pressure gauge, thermowell, dip tube with valve, and a vapor valve, 105.14 grams (0.36 mole) of 1,1,1,2,3,3,3-heptafluoro-2-iodopropane (Matrix Scientific P.O. Box 25067 Columbia S.C. 92994-5067) and 10 grams (0.36 mole) of ethylene to form a mixture. The mixture can be heated to about 180° C. for about 6 hours. The mixture can be allowed to cooled to afford 105.99 grams of the crude monoadduct product (86 area % by gc) 1,1,1,2-tetrafluoro-2-(trifluoromethyl)-4-iodobutane and minor amounts of both the diadduct product 1,1,1,2-tetrafluoro-2-(trifluoromethyl)-6-iodohexane and the triadduct product 1,1,1,2-tetrafluoro-2-(trifluoromethyl)-8-iodooctane. The monoadduct product can be distilled at 56° C./96 torr. The product structure(s) can be confirmed by NMR analysis. The 1,1,1,2-tetrafluoro-2-(trifluoromethyl)-4-iodobutane can also be obtained from Matrix Scientific P.O. Box 25067 Columbia S.C. 92994-5067.

In further accordance with scheme (1) above, in a flask that can be equipped with an agitator, thermocouple, cold product trap, and an addition funnel, 64 grams (1.14 moles) of potassium hydroxide and about 240 mL of methanol can be placed to form a mixture. The mixture can then be heated to from about 45° C. to about 55° C. followed by the drop wise addition of 244.6 grams (0.75 mole) of 1,1,1,2-tetrafluoro-2-(trifluoromethyl)-4-iodobutane to form a reaction mixture. In the cold product trap can be collected, 144.8 grams of 3,4,4,4-tetrafluoro-3-(trifluoromethyl)but-1-ene product of about 93 percent purity by gas chromotography. The product structure can be confirmed by NMR analysis.

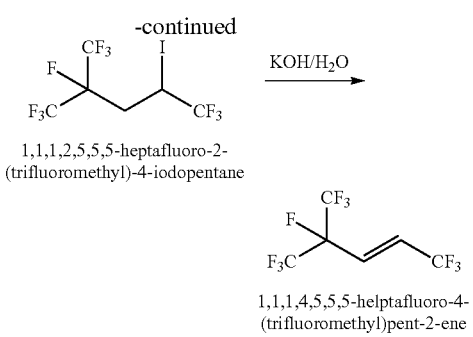

Referring to scheme (2) above, in a 2 L autoclave that can be equipped with a rupture disc, pressure gauge, dip tube with valve, vapor valve, cooling loop, and thermowell, 1035 grams (3.5 moles) of 1,1,1,2,3,3,3-heptafluoro-2-iodopropane can be placed. The autoclave can be sealed with stirring at room temperature. To the 1,1,1,2,3,3,3-heptafluoro-2-iodopropane, 339 grams (3.5 mole) of 3,3,3-trifluoropropene can be fed via the dip tube to form a mixture. The mixture can be heated to about 180° C. wherein the autoclave pressure, which can be about 600 psig, can be observed to decrease. The reaction can be observed to be complete at which time the autoclave pressure stabilizes. The mixture can be collected and analyzed by gas chromatography to afford the following distribution: 10.3% of the starting material 3,3,3-trifluoropropene, 12.0% of the starting material 1,1,1,2,3,3,3-heptafluoro-2-iodopropane, 62.3% of the monoadduct product 1,1,1,2,5,5,5-heptafluoro-2-(trifluoromethyl)-4-iodopentane, and 12.4% of the diadduct product 1,1,1,2,7,7,7-heptafluoro-2,4-bis(trifluoromethyl)-6-iodoheptane.

In reference to scheme (2) above, in a flask that can be equipped with a material feeding tube coupled to a syringe pump, a thermocouple, and a simple distillation apparatus that can include a Vigureux column, a reflux condenser, thermocouple, angled vacuum connection adaptor that can be coupled to a dry ice/acetone trap, and a receiver flask, 419 grams of a 32 (wt/wt) percent KOH solution, and 9.6 grams of methyl tributylammonium chloride can be placed to form a mixture. Into the syringe pump, 215.41 grams (0.55 mole) of 1,1,1,2,5,5,5-heptafluoro-2-(trifluoromethyl)-4-iodopentane can be placed. The mixture can be heated to from about 75° C. to about 100° C. whereupon 1,1,1,2,5,5,5-heptafluoro-2-(trifluoromethyl)-4-iodopentane can be added to form a reaction mixture over a period of about 160 minutes. 1,1,1,4,5,5,5-heptafluoro-4-(trifluoromethyl)pent-2-ene product can be collected in the receiver flask in concert with the addition of the starting material. The reaction mixture can be additionally heated to from about 75° C. to about 100° C. to drive the product from the reaction mixture into the receiver flask. The receiver flask can be emptied to afford 118.24 grams of 1,1,1,4,5,5,5-heptafluoro-4-(trifluoromethyl)pent-2-ene product. The product structure can be confirmed by NMR analysis.

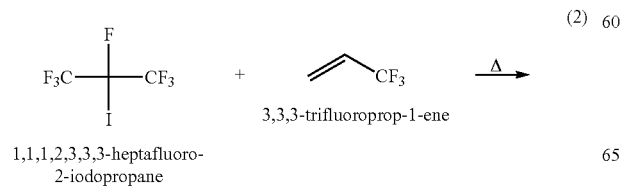

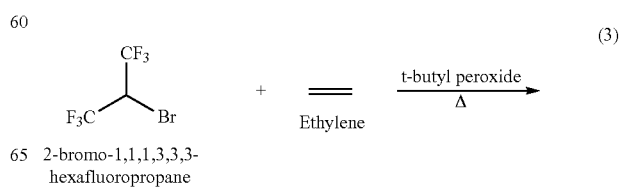

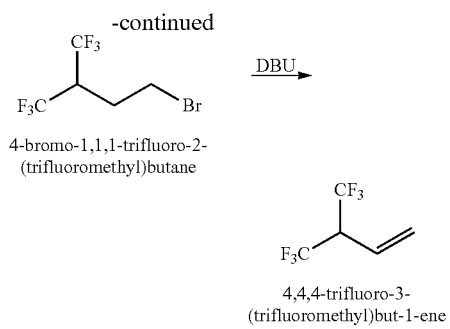

4-bromo-1,1,1-trifluoro-2-(trifluoromethyl)butane 4,4,4-trifluoro-3-(trifluoromethyl)but-1-ene According to scheme (3) above, in a 300 cc autoclave that can be equipped with an agitator, rupture disc, pressure gauge, thermocouple, dip tube with valve, and vapor valve, 280.0 grams (1.2124 moles) of 2-bromo-1,1,1,3,3,3-hexafluoropropane (refer to scheme (25) below) and 2.9 grams (0.0198 mole) of tert-butyl peroxide can be placed to form a mixture. The reactor can be sealed and with stirring, heated to 120° C. To the mixture, ethylene can be added to form a reaction mixture until the autoclave pressure reaches about 200 psig whereupon a slight exotherm can be observed coupled with a decrease in autoclave pressure. Ethylene can be added continually until an equal molar amount with respect to the 2-bromo-1,1,1,3,3,3-hexafluoropropane has been added. The reaction mixture can be distilled to afford 131.4 grams of the 4-bromo-1,1,1-trifluoro-2-(trifluoromethyl)butane product and a minor amount of a diadduct 6-bromo-1,1,1-trifluoro-2-(trifluoromethyl)hexane. The product structure can be confirmed by GC/MS and/or NMR analysis.

In accordance with scheme (3) above, in a flask that can be equipped with an agitator, thermometer, addition funnel, and Vigreux column with Claisen side arm equipped with condenser, thermometer, and receiver flask, 18.6 grams (0.0718 mole) of 4-bromo-1,1,1-trifluoro-2-(trifluoromethyl)butane and 20.4 grams of methylene chloride can be placed to form a mixture. To the mixture, 18.3 grams (0.12 mole) of 2,3,4,6,7,8,9,10-octahydropyrimido[1,2-a]azepine (DBU) can be added drop wise to form a reaction mixture. The product, 4,4,4-trifluoro-3-(trifluoromethyl)but-1-ene, can be collected in the receiving flask simultaneous to the DBU addition. The reaction mixture can be heated until methylene chloride begins to collect in the receiving flask. The product structure can be confirmed by GC/MS and/or NMR analysis.

(4)

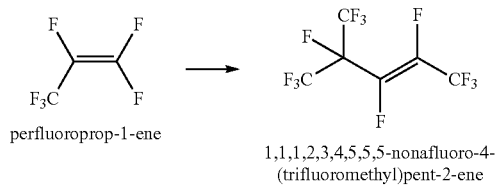

perfluoroprop-1-ene 1,1,1,2,3,4,5,5,5-nonafluoro-4-(trifluoromethyl)pent-2-ene

In accordance with scheme (4) above perfluoroprop-1-ene (Synquest Laboratories Inc. P.O. Box 309 Alachua, Fla. 32616-0309) can be dimerized in the presence of an organic solvent, a halide compound, and a crown ether in the liquid phase. In another embodiment, the dimerization can be performed by heating perfluoroprop-1-ene over carbon in the gas phase.

(5)

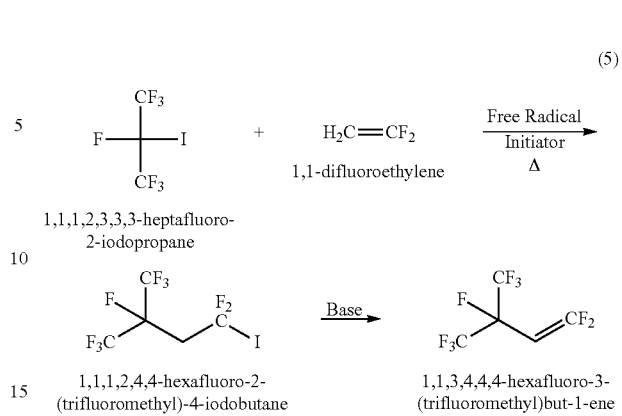

1,1,1,2,3,3,3-heptafluoro-2-iodopropane 1,1,1,2,4,4-hexafluoro-2-(trifluoromethyl)-4-iodobutane 1,1,3,4,4,4-hexafluoro-3-(trifluoromethyl)but-1-ene In accordance with scheme (5) above, in a 300 cc autoclave that can be equipped with an agitator, rupture disc, pressure gauge, thermowell, dip tube with valve, and a vapor valve, 136.0 grams (0.4596 mole) of 1,1,1,2,3,3,3-heptafluoro-2-iodopropane and 3.2 grams (0.022 mole) of tert-butyl peroxide can be placed to form a mixture. The mixture can be heated to about 120° C. To the mixture, a sufficient amount of 1,1-difluoroethylene can be added to bring the autoclave pressure to about 150 psig and form a reaction mixture whereupon an exotherm can be observed. As the reaction proceeds, the autoclave pressure can be observed to decrease necessitating the addition of additional 1,1-difluoroethylene to the system. The total amount of 1,1-difluoroethene added to the autoclave can be about 57 grams (0.8901 mole). The reaction mixture can be distilled to afford 85.8 grams of the product 1,1,1,2,4,4-hexafluoro-2-(trifluoromethyl)-4-iodobutane and 52.5 grams of a diadduct product 1,1,1,2,4,4,6,6-octafluoro-2-(trifluoromethyl)-6-iodohexane and a minor amount of a triadduct 1,1,1,2,4,4,6,6,8,8-decafluoro-2-(trifluoromethyl)-8-iodooctane. The product structure(s) can be confirmed by GC/MS and/or NMR analysis.

In accordance with scheme (5) above, in a flask that can be equipped with an agitator, thermometer, addition funnel, and Vigreux column with Claisen side arm equipped with condenser, thermometer, and receiver flask, 45.6 grams of a 30 (wt/wt) % KOH solution and 3.6 grams of methyltributylammonium chloride can be placed to form a mixture and heated to about 96° C. To the mixture, 38.1 grams (0.1058 mole) of 1,1,1,2,4,4-hexafluoro-2-(trifluoromethyl)-4-iodobutane can be added drop wise to form a reaction mixture. Immediately upon addition of the 1,1,1,2,4,4-hexafluoro-2-(trifluoromethyl)-4-iodobutane to the mixture, 1,1,3,4,4,4-hexafluoro-3-(trifluoromethyl)but-1-ene can be observed to collect in the receiver flask. The collected material can be further purified to afford 10.2 grams of the desired product 1,1,3,4,4,4-hexafluoro-3-(trifluoromethyl)but-1-ene. The product structure can be confirmed by GC/MS and/or NMR analysis.

(6)

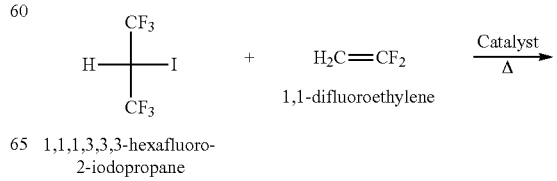

1,1,1,3,3,3-hexafluoro-2-iodopropane 1,1-difluoroethylene

-continued

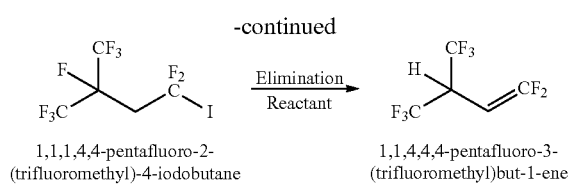

1,1,1,4-pentafluoro-2-
(trifluoromethyl)-4-iodobutane 1,1,4,4,4-pentafluoro-3-
(trifluoromethyl)but-1-ene In accordance with scheme (6) above, in a 300 cc autoclave that can be equipped with an agitator, rupture disc, pressure gauge, thermowell, dip tube with valve, and a vapor valve, an amount of 1,1,1,3,3,3-hexafluoro-2-iodopropane and a sufficient amount of catalyst can be placed to form a mixture. The mixture can be heated to from about 60° to about 190° C. To the mixture, a sufficient amount of 1,1-difluoroethylene can be added to form a reaction mixture. The total amount of 1,1-difluoroethylene added to the autoclave can be about the molar equivalent of 1,1,1,3,3,3-hexafluoro-2-iodopropane. The reaction mixture can be distilled to afford the product 1,1,1,4-pentafluoro-2-(trifluoromethyl)-4-iodobutane. The product structure can be confirmed by GC/MS and/or NMR analysis.

In accordance with scheme (6) above, in a flask that can be equipped with an agitator, thermometer, addition funnel, and Vigreux column with Claisen side arm equipped with condenser, thermometer, and receiver flask, a sufficient amount of catalyst and of a phase transfer catalyst can be placed to form a mixture and heated to from about 25° C. to about 100° C. To the mixture, an amount of 1,1,1,4,4-pentafluoro-2-(trifluoromethyl)-4-iodobutane can be added drop wise to form a reaction mixture. Upon addition of the 1,1,1,2,4,4-hexafluoro-2-(trifluoromethyl)-4-iodobutane to the mixture, the product 1,1,4,4,4-pentafluoro-3-(trifluoromethyl)but-1-ene can be collected in the receiver flask. The product can be further purified by distillation. The product structure can be confirmed by GC/MS and/or NMR analysis.

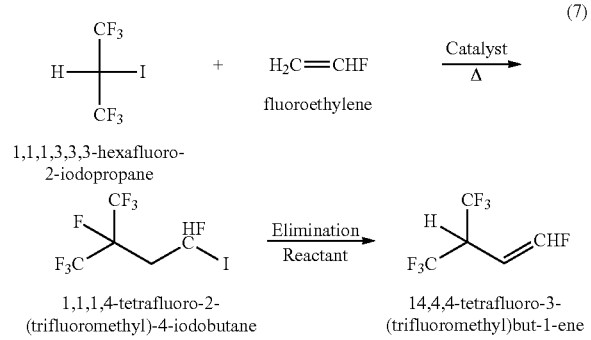

(7)

1,1,1,3,3,3-hexafluoro-
2-iodopropane 1,1,1,4-tetrafluoro-2-
(trifluoromethyl)-4-iodobutane 14,4,4-tetrafluoro-3-
(trifluoromethyl)but-1-ene In accordance with scheme (7) above, in a 300 cc autoclave that can be equipped with an agitator, rupture disc, pressure gauge, thermowell, dip tube with valve, and a vapor valve, an amount of 1,1,1,3,3,3-hexafluoro-2-iodopropane and a sufficient amount of catalyst can be placed to form a mixture. The mixture can be heated to from about 60° C. to about 190° C. To the mixture, a sufficient amount of fluoroethylene can be added to form a reaction mixture. The total amount of fluoroethylene added to the autoclave can be about the molar equivalent of 1,1,1,3,3,3-hexafluoro-2-iodopropane. The reaction mixture can be distilled to afford the product 1,1,1,4-tetrafluoro-2-(trifluoromethyl)-4-iodobutane. The product structure can be confirmed by GC/MS and/or NMR analysis.

In accordance with scheme (7) above, in a flask equipped with magnetic stirring, thermometer, addition funnel, and Vigreux column with Claisen side arm equipped with condenser, thermometer, and receiver flask, an amount of an elimination reactant and of a phase transfer catalyst can be placed to form a mixture and heated to from about 25° C. to about 100° C. To the mixture, an amount of 1,1,1,4-tetrafluoro-2-(trifluoromethyl)-4-iodobutane can be added drop wise to form a reaction mixture. Upon addition of the 1,1,1,4-tetrafluoro-2-(trifluoromethyl)-4-iodobutane to the mixture, the product 1,4,4,4-tetrafluoro-3-(trifluoromethyl)but-1-ene can be collected in the receiver flask. The product can be further purified by distillation. The product structure can be confirmed by GC/MS and/or NMR analysis.

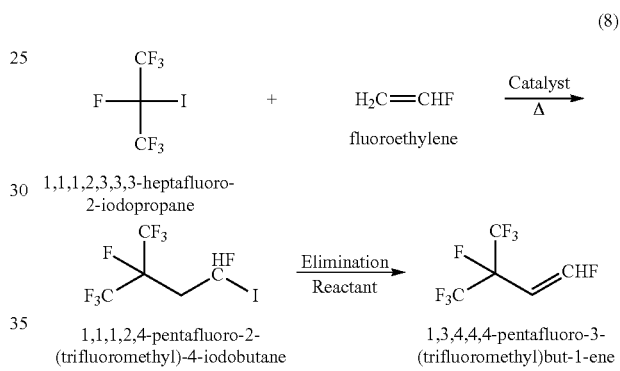

(8)

1,1,1,2,3,3,3-heptafluoro-
2-iodopropane 1,1,1,2,4-pentafluoro-2-
(trifluoromethyl)-4-iodobutane 1,3,4,4,4-pentafluoro-3-
(trifluoromethyl)but-1-ene In accordance with scheme (8) above, in a 300 cc autoclave that can be equipped with an agitator, rupture disc, pressure gauge, thermowell, dip tube with valve, and a vapor valve, an amount of 1,1,1,2,3,3,3-heptafluoro-2-iodopropane and a sufficient amount of catalyst can be placed to form a mixture. The mixture can be heated to from about 60° C. to about 190° C. To the mixture, a sufficient amount of fluoroethylene can be added to form a reaction mixture. The total amount of fluoroethylene added to the autoclave can be about the molar equivalent of 1,1,1,2,3,3,3-heptafluoro-2-iodopropane. The reaction mixture can be distilled to afford the product 1,1,1,2,4-pentafluoro-2-(trifluoromethyl)-4-iodobutane. The product structure can be confirmed by GC/MS and/or NMR analysis.

In accordance with scheme (8) above, in a flask equipped with an agitator, thermometer, addition funnel, and Vigreux column with Claisen side arm equipped with condenser, thermometer, and receiver flask, a sufficient amount of elimination reactant and of a phase transfer catalyst can be placed to form a mixture and heated to from about 25° C. to about 100° C. To the mixture, an amount of 1,1,1,2,4-pentafluoro-2-(trifluoromethyl)-4-iodobutane can be added drop wise to form a reaction mixture. Upon addition of the 1,1,1,2,4-pentafluoro-2-(trifluoromethyl)-4-iodobutane to the mixture, the product 1,3,4,4,4-pentafluoro-3-(trifluoromethyl)but-1-ene can be collected in the receiver flask. The product can be further purified by distillation. The product structure can be confirmed by GC/MS and/or NMR analysis.

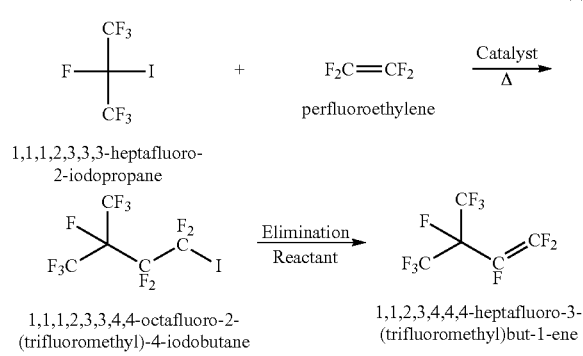

1,1,1,2,3,3,3-heptafluoro-2-iodopropane + perfluoroethylene →(Catalyst, Δ) 1,1,1,2,3,3,4,4-octafluoro-2-(trifluoromethyl)-4-iodobutane →(Elimination Reactant) 1,1,2,3,4,4,4-heptafluoro-3-(trifluoromethyl)but-1-ene  (9)

In accordance with scheme (9) above, in a 300 cc autoclave that can be equipped with an agitator, rupture disc, pressure gauge, thermowell, dip tube with valve, and a vapor valve, an amount of 1,1,1,2,3,3,3-heptafluoro-2-iodopropane and a sufficient amount of catalyst can be placed to form a mixture. The mixture can be heated to from about 60° C. to about 190° C. To the mixture, a sufficient amount of perfluoroethylene can be added to form a reaction mixture. The total amount of perfluoroethylene added to the autoclave can be about the molar equivalent of 1,1,1,2,3,3,3-heptafluoro-2-iodopropane. The reaction mixture can be distilled to afford the product 1,1,1,2,3,3,4,4-octafluoro-2-(trifluoromethyl)-4-iodobutane. The product structure can be confirmed by GC/MS and/or NMR analysis.

In accordance with scheme (9) above, in a flask equipped with an agitator, thermometer, addition funnel, and Vigreux column with Claisen side arm equipped with condenser, thermometer, and receiver flask, an amount of elimination reactant and of a phase transfer catalyst can be placed to form a mixture and heated to from about 25° C. to about 100° C. To the mixture, an amount of 1,1,1,2,3,3,4,4-octafluoro-2-(trifluoromethyl)-4-iodobutane can be added drop wise to form a reaction mixture. Upon addition of the 1,1,1,2,3,3,4,4-octafluoro-2-(trifluoromethyl)-4-iodobutane to the mixture, 1,1,2,3,4,4,4-heptafluoro-3-(trifluoromethyl)but-1-ene can be formed in the receiver flask. The collected material can be further purified to afford an amount of the desired product 1,1,2,3,4,4,4-heptafluoro-3-(trifluoromethyl)but-1-ene. The product structure can be confirmed by GC/MS and/or NMR analysis.

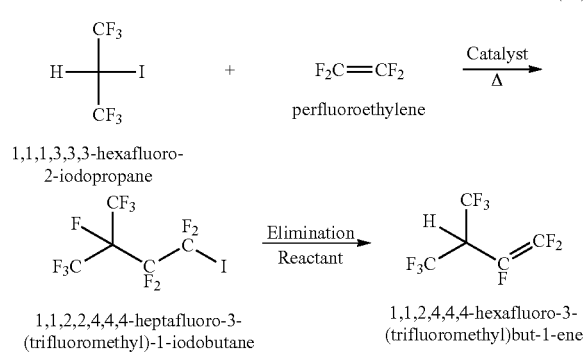

1,1,1,3,3,3-hexafluoro-2-iodopropane + perfluoroethylene →(Catalyst, Δ) 1,1,2,2,4,4,4-heptafluoro-3-(trifluoromethyl)-1-iodobutane →(Elimination Reactant) 1,1,2,4,4,4-hexafluoro-3-(trifluoromethyl)but-1-ene  (10)

In accordance with scheme (10) above, in a 300 cc autoclave that can be equipped with an agitator, rupture disc, pressure gauge, thermowell, dip tube with valve, and a vapor valve, an amount of 1,1,1,3,3,3-hexafluoro-2-iodopropane and a sufficient amount of catalyst can be placed to form a mixture. The mixture can be heated to from about 60° C. to about 190° C. To the mixture, a sufficient amount of perfluoroethylene can be added to form a reaction mixture. The total amount of perfluoroethylene added to the autoclave can be about the molar equivalent of 1,1,1,3,3,3-hexafluoro-2-iodopropane. The reaction mixture can be distilled to afford the product 1,1,2,2,4,4,4-heptafluoro-2-(trifluoromethyl)-4-iodobutane. The product structure can be confirmed by GC/MS and/or NMR analysis.

In accordance with scheme (10) above, in a flask equipped with an agitator, thermometer, addition funnel, and Vigreux column with Claisen side arm equipped with condenser, thermometer, and receiver flask, an amount of an elimination reactant and of a phase transfer catalyst can be placed to form a mixture and heated to from about 25° C. to about 100° C. To the mixture, an amount of 1,1,2,2,4,4,4-heptafluoro-2-(trifluoromethyl)-4-iodobutane can be added drop wise to form a reaction mixture. Upon addition of the 1,1,2,2,4,4,4-heptafluoro-2-(trifluoromethyl)-4-iodobutane to the mixture, the product 1,1,2,4,4,4-hexafluoro-3-(trifluoromethyl)but-1-ene can be collected in the receiver flask. The product can be further purified by distillation. The product structure can be confirmed by GC/MS and/or NMR analysis.

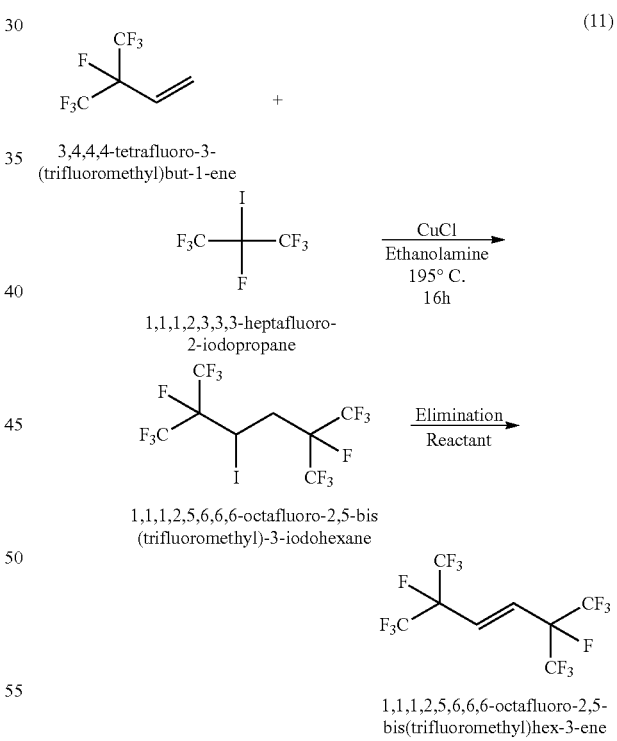

3,4,4,4-tetrafluoro-3-(trifluoromethyl)but-1-ene + 1,1,1,2,3,3,3-heptafluoro-2-iodopropane →(CuCl, Ethanolamine, 195° C., 16h) 1,1,1,2,5,6,6,6-octafluoro-2,5-bis(trifluoromethyl)-3-iodohexane →(Elimination Reactant) 1,1,1,2,5,6,6,6-octafluoro-2,5-bis(trifluoromethyl)hex-3-ene  (11)

According to scheme (11) above, in a 300 mL stainless steel autoclave that can be equipped with an agitator, venting valve, thermocouple, rupture disk, and a pressure gauge, 25 grams (0.13 mole) of 3,4,4,4-tetrafluoro-3-(trifluoromethyl)but-1-ene (refer to scheme (1) above), 75 grams (0.25 mole) of 1,1,1,2,3,3,3-heptafluoro-2-iodopropane, 0.15 grams (0.0015 mole) of copper (I) chloride, and 0.75 grams (0.012 mole) of ethanolamine can be placed to form a mixture. The mixture can be heated to about 195° C. and held for about 16 hours to afford the intermediate product 1,1,1,2,5,6,6,6-octafluoro-2,5-bis(trifluoromethyl)-3-iodohexane. The intermediate product structure can be confirmed by GC/MS and/or NMR analysis.

In further accordance with scheme (11) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, about 20 grams (0.041 mole) of 1,1,1,2,5,6,6,6-octafluoro-2,5-bis(trifluoromethyl)-3-iodohexane can be added drop wise to form a mixture. Immediately upon addition of the 1,1,1,2,5,6,6,6-octafluoro-2,5-bis(trifluoromethyl)-3-iodohexane to the mixture, the product 1,1,1,2,5,6,6,6-octafluoro-2,5-bis(trifluoromethyl)hex-3-ene can be observed to collect in the receiver flask. The product can be further purified by distillation and the structure can be confirmed by GC/MS and/or NMR analysis.

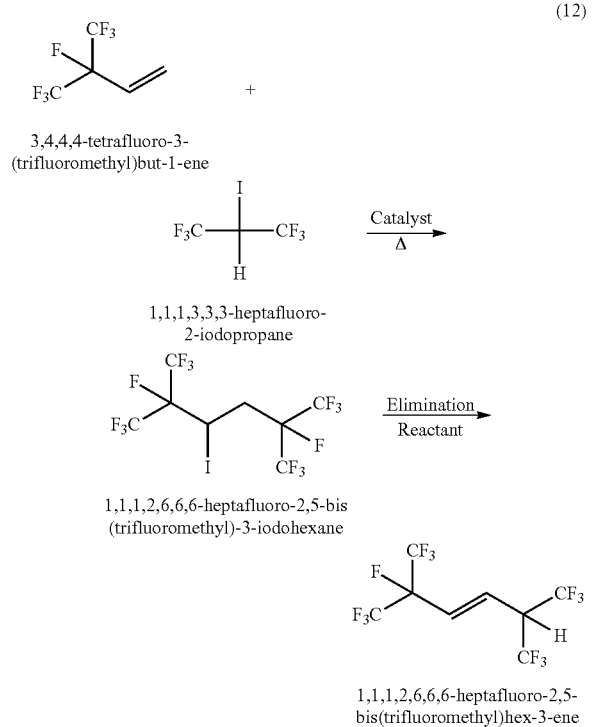

Referring to scheme (12) above, in a 300 mL stainless steel autoclave that can be equipped with an agitator, venting valve, thermocouple, rupture disk, and a pressure gauge, a sufficient amount of 3,4,4,4-tetrafluoro-3-(trifluoromethyl)but-1-ene (refer to scheme (1) above), a sufficient amount of 1,1,1,3,3,3-hexafluoro-2-iodopropane, and a sufficient amount of a catalyst can be placed to form a mixture. The mixture can be heated to from about 60° C. to about 195° C. and held for from about 15 hours to about 21 hours, and/or about 18 hours to afford the intermediate product 1,1,1,2,5,6,6,6-octafluoro-2,5-bis(trifluoromethyl)-3-iodohexane. The intermediate product structure can be confirmed by GC/MS and/or NMR analysis.

In further reference to scheme (12) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,5,6,6,6-octafluoro-2,5-bis(trifluoromethyl)-3-iodohexane can be added drop wise to form a mixture. Immediately upon addition of the 1,1,1,2,5,6,6,6-octafluoro-2,5-bis(trifluoromethyl)-3-iodohexane to the mixture, the product 1,1,1,2,6,6,6-heptafluoro-2,5-bis(trifluoromethyl)hex-3-ene can be observed to collect in the receiver flask. The product can be further purified by distillation and the structure can be confirmed by GC/MS and/or NMR analysis.

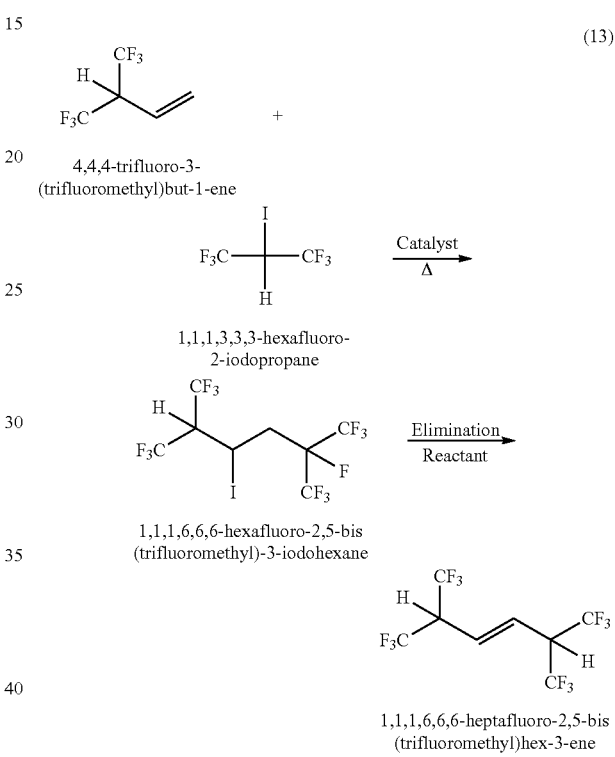

Referring to scheme (13) above, in a 300 mL stainless steel autoclave that can be equipped with an agitator, venting valve, thermocouple, rupture disk, and a pressure gauge, a sufficient amount of 4,4,4-trifluoro-3-(trifluoromethyl)but-1-ene (refer to scheme (3) above), a sufficient amount of 1,1,1,3,3,3-hexafluoro-2-iodopropane, and a sufficient amount of a catalyst can be placed to form a mixture. The mixture can be heated to from about 60° C. to about 195° C. and held for from about 15 hours to about 21 hours, and/or about 18 hours to afford the intermediate product 1,1,1,6,6,6-hexafluoro-2,5-bis(trifluoromethyl)-3-iodohexane. The intermediate product structure can be confirmed by GC/MS and/or NMR analysis.

In further reference to scheme (13) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1 1,1,1,6,6,6-hexafluoro-2,5-bis(trifluoromethyl)-3-iodohexane can be added drop wise to form a mixture. Immediately upon addition of the 1,1,1,6,6,6-hexafluoro-2,5-bis(trifluoromethyl)-3-iodohexane to the mixture, the product 1,1,1,6,6,6-hexafluoro-2,5-bis (trifluoromethyl)hex-3-ene can be observed to collect in the receiver flask. The product can be further purified by distillation and the structure can be confirmed by GC/MS and/or NMR analysis.

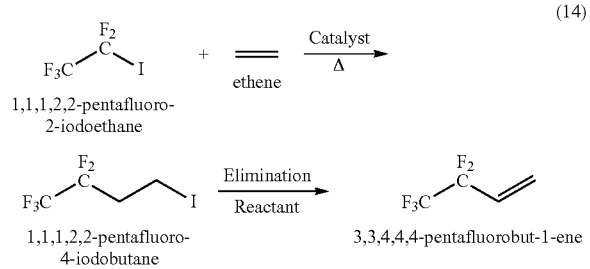

(14)

In accordance with scheme (14), in a 300 cc autoclave that can be equipped with mechanical stirring, rupture disc, pressure gauge, thermowell, dip tube with valve, and a vapor valve, a sufficient amount of 1,1,1,2,2-pentafluoro-2-iodoethane (Matrix Scientific P.O. Box 25067 Columbia S.C. 92994-5067) and of ethylene can be added to form a mixture. The mixture can be heated to from about 60° C. to about 195° C. and held for from about 15 hours to about 21 hours, and/or about 18 hours. The mixture can be allowed to cool to afford the crude product 1,1,1,2,2-pentafluoro-4-iodobutane. The product can be purified by distillation and the product structure can be confirmed by NMR analysis.

In further accordance with scheme (14) above, in a flask that can be equipped with an agitator, thermocouple, cold product trap, and an addition funnel, a sufficient amount of an elimination reactant can be placed to form a mixture. The mixture can then be heated to from about 25° C. to about 100° C. followed by the drop wise addition of 1,1,1,2,2-pentafluoro-4-iodobutane to form a reaction mixture. In the cold product trap, the product 3,3,4,4,4-pentafluorobut-1-ene can be collected. The product structure can be confirmed by NMR analysis.

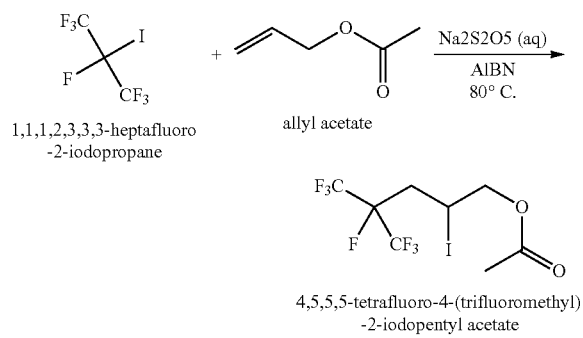

(15)

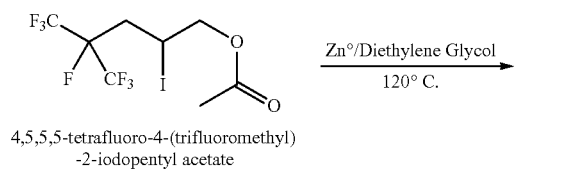

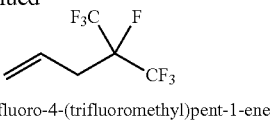

4,5,5,5-tetrafluoro-4-(trifluoromethyl)pent-1-ene

Referring to scheme (15) above, AIBN (9.2 g, 0.06 mole), 1,1,1,2,3,3,3-heptafluoro-2-iodopropane (1651 grams, 5.6 mole), and 293 grams of 30% (wt/wt) aqueous $Na_2S_2O_5$ can be placed into a 2 L pressure reactor to form a mixture. The reactor can be sealed and heated to 80° C. under autogeneous pressure. Allyl acetate (587 grams, 5.9 mole) can be slowly added to this mixture and the mixture can be stirred for an additional 4 hours. After stirring, an organic layer can be observed, removed, washed twice with $H_2O$, and dried with $MgSO_4$ to give 2212 g of 94% (area percent by gas chromatography) the $R_F$-intermediate 4,5,5,5-tetrafluoro-4-(trifluoromethyl)-2-iodopentyl acetate.

Diethylene glycol (2944 grams) and zinc powder (1330 grams) can be placed into a 5 L 5-neck flask equipped with a simple distillation apparatus to form a mixture. This mixture can be stirred and heated to 120° C. and the 4,5,5,5-tetrafluoro-4-(trifluoromethyl)-2-iodopentyl acetate (4149 grams) can be slowly added. As the 4,5,5,5-tetrafluoro-4-(trifluoromethyl)-2-iodopentyl acetate is added, the $R_F$-intermediate 4,5,5,5-tetrafluoro-4-(trifluoromethyl)pent-1-ene (2075 grams) can be flashed-off and collected in a 1 L ice trap. The contents of the ice trap can be distilled to give 4,5,5,5-tetrafluoro-4-(trifluoromethyl)pent-1-ene >99.5% (area percent by gas chromatography) (b.p. 54° C.).

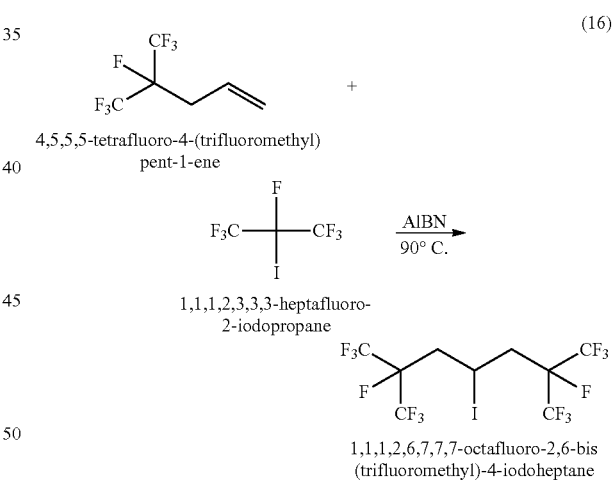

(16)

Referring to scheme (16) above, 20 grams (0.095 mole) of 4,5,5,5-tetrafluoro-4-(trifluoromethyl)pent-1-ene (refer to scheme (15) above) and 28.18 grams (0.095 mole) 1,1,1,2,3,3,3-heptafluoro-2-iodopropane can be provided to a glass pressure tube to form a mixture. To the mixture, 0.51 gram of azobisisobutyronitrile (AIBN) can be added to form a reaction mixture. The reaction mixture can be heated to and maintained at about 85° C. for about 24 hours. During heating, additional AIBN can be added (0.11 grams after 3 hours and another 0.1 grams after 21 hours). The mixture can then be washed twice with $H_2O$ to afford the product 1,1,1,2,6,7,7,7-octafluoro-2,6-bis(trifluoromethyl)-4-iodoheptane and analysis via gas chromatography can yield a 56% area percent purity.

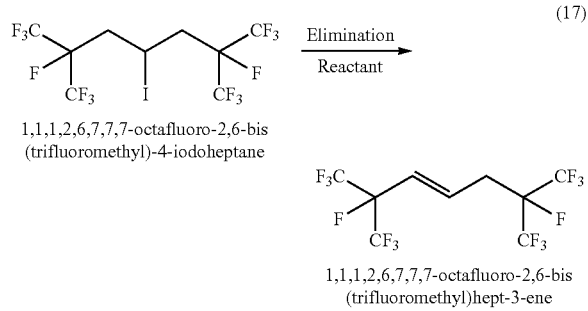

(17)

1,1,1,2,6,7,7,7-octafluoro-2,6-bis(trifluoromethyl)-4-iodoheptane 1,1,1,2,6,7,7,7-octafluoro-2,6-bis(trifluoromethyl)hept-3-ene In accordance with scheme (17) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,7,7,7-octafluoro-2,6-bis(trifluoromethyl)-4-iodoheptane (refer to scheme (16) above) can be added drop wise to form a mixture. Immediately upon addition of the 1,1,1,2,6,7,7,7-octafluoro-2,6-bis(trifluoromethyl)-4-iodoheptane to the mixture, the product 1,1,1,2,6,7,7,7-octafluoro-2,6-bis(trifluoromethyl)hept-3-ene can be observed to collect in the receiver flask. The product can be further purified by distillation and the structure can be confirmed by GC/MS and/or NMR analysis.

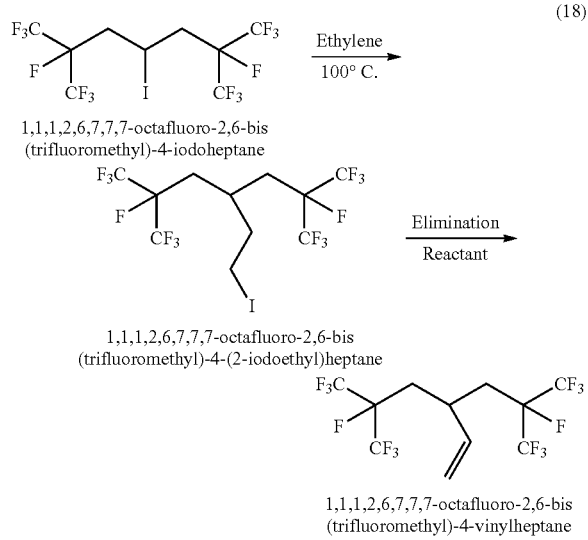

(18)

1,1,1,2,6,7,7,7-octafluoro-2,6-bis(trifluoromethyl)-4-iodoheptane 1,1,1,2,6,7,7,7-octafluoro-2,6-bis(trifluoromethyl)-4-(2-iodoethyl)heptane 1,1,1,2,6,7,7,7-octafluoro-2,6-bis(trifluoromethyl)-4-vinylheptane According to scheme (18) above, into a 300 mL autoclave that can be equipped with a dip tube, thermocouple, agitator, pressure gauge, and an attachment to a reservoir containing ethylene gas, 319 grams (0.63 mole) 1,1,1,2,6,7,7,7-octafluoro-2,6-bis(trifluoromethyl)-4-iodoheptane (refer to scheme (16) above) and 3 grams (0.012 mole) dibenzoyl peroxide can be added to form a mixture. The autoclave can then be sealed, evacuated, and heated to about 100° C. Ethylene gas can be added to the mixture to form a reaction mixture. The reaction mixture can be held at a pressure of about 380 psig for about four hours. The reaction mixture can then be chilled using an ice water bath and degassed. To the reaction mixture, an additional 3.0 grams (0.012 mole) dibenzoyl peroxide can be added to form a new mixture. The autoclave can then be sealed, evacuated, and heated to about 100° C. Ethylene gas can be added to the mixture to form a new reaction mixture. The new reaction mixture can be held at a pressure of about 380 psig for about four hours then chilled with an ice water bath, degassed, and opened to provide 336.5 grams of 80 (wt/wt) percent pure (by gas chromatography) 1,1,1,2,6,7,7,7-octafluoro-2,6-bis(trifluoromethyl)-4-iodoheptane product. The product can be purified by vacuum distillation (b.p. 53° C./1.3 Torr) the structure confirmed by NMR analysis.

In further accordance with scheme (18) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,7,7,7-octafluoro-2,6-bis(trifluoromethyl)-4-(2-iodoethyl)heptane can be added drop wise to form a mixture. Immediately upon addition of the 1,1,1,2,6,7,7,7-octafluoro-2,6-bis(trifluoromethyl)-4-(2-iodoethyl)heptane to the mixture, the product 1,1,1,2,6,7,7,7-octafluoro-2,6-bis(trifluoromethyl)-4-vinylheptane can be observed to collect in the receiver flask. The product can be further purified by distillation and the structure can be confirmed by GC/MS and/or NMR analysis.

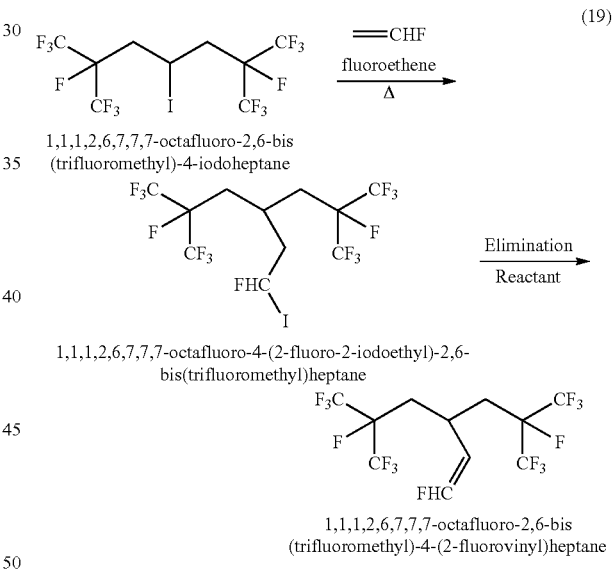

(19)

1,1,1,2,6,7,7,7-octafluoro-2,6-bis(trifluoromethyl)-4-iodoheptane 1,1,1,2,6,7,7,7-octafluoro-4-(2-fluoro-2-iodoethyl)-2,6-bis(trifluoromethyl)heptane 1,1,1,2,6,7,7,7-octafluoro-2,6-bis(trifluoromethyl)-4-(2-fluorovinyl)heptane According to scheme (19) above, into an autoclave that can be equipped with a dip tube, thermocouple, agitator, pressure gauge, and an attachment to a reservoir containing fluoroethylene gas, an amount of 1,1,1,2,6,7,7,7-octafluoro-2,6-bis(trifluoromethyl)-4-iodoheptane (refer to scheme (16) above) and a sufficient amount of catalyst can be added to form a mixture. The autoclave can then be sealed, evacuated, and heated to from about 50° C. to about 120° C. Fluoroethylene gas can be added to the mixture to form a reaction mixture. The reaction mixture can be held at a sufficient pressure for from about four hours to about 16 hours. The reaction mixture can then be chilled using an ice water bath and degassed to provide 1,1,1,2,6,7,7,7-octafluoro-4-(2-fluoro-2-iodoethyl)-2,6-bis(trifluoromethyl)heptane product. The product can be purified by vacuum distillation and the structure confirmed by NMR analysis.

In further accordance with scheme (19) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,7,7,7-octafluoro-4-(2-fluoro-2-iodoethyl)-2,6-bis(trifluoromethyl)heptane can be added drop wise to form a mixture. Immediately upon addition of the 1,1,1,2,6,7,7,7-octafluoro-4-(2-fluoro-2-iodoethyl)-2,6-bis(trifluoromethyl)heptane to the mixture, the product 1,1,1,2,6,7,7,7-octafluoro-2,6-bis(trifluoromethyl)-4-(2-fluorovinyl)heptane can be observed to collect in the receiver flask. The product can be further purified by distillation and the structure can be confirmed by GC/MS and/or NMR analysis.

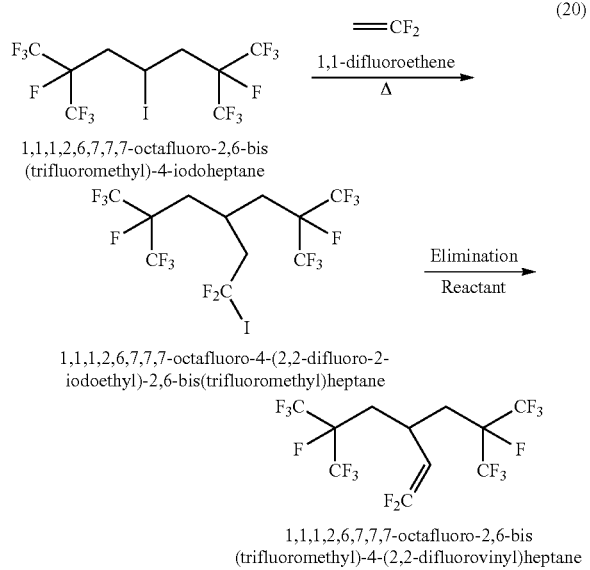

According to scheme (20) above, into an autoclave that can be equipped with a dip tube, thermocouple, agitator, pressure gauge, and an attachment to a reservoir containing 1,1-difluoroethylene gas, an amount of 1,1,1,2,6,7,7,7-octafluoro-2,6-bis(trifluoromethyl)-4-iodoheptane (refer to scheme (16) above) and an sufficient amount of catalyst can be added to form a mixture. The autoclave can then be sealed, evacuated, and heated to from about 50° C. to about 120° C. 1,1-fluoroethylene gas can be added to the mixture to form a reaction mixture. The reaction mixture can be held at a sufficient pressure for from about four hours to about 16 hours. The reaction mixture can then be chilled using an ice water bath and degassed to provide 1,1,1,2,6,7,7,7-octafluoro-4-(2,2-difluoro-2-iodoethyl)-2,6-bis(trifluoromethyl)heptane product. The product can be purified by vacuum distillation and the structure confirmed by NMR analysis.

In further accordance with scheme (20) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,7,7,7-octafluoro-4-(2,2-difluoro-2-iodoethyl)-2,6-bis(trifluoromethyl)heptane can be added drop wise to form a mixture. Immediately upon addition of the 1,1,1,2,6,7,7,7-octafluoro-4-(2,2-difluoro-2-iodoethyl)-2,6-bis(trifluoromethyl)heptane to the mixture, the product 1,1,1,2,6,7,7,7-octafluoro-2,6-bis(trifluoromethyl)-4-(2,2-difluorovinyl)heptane can be observed to collect in the receiver flask. The product can be further purified by distillation and the structure can be confirmed by GC/MS and/or NMR analysis.

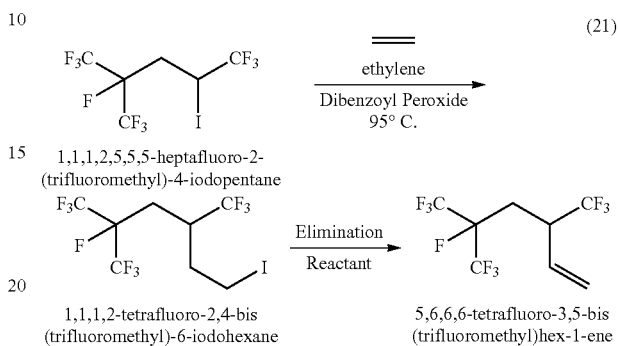

Referring to scheme (21) above, in a 20 mL autoclave that can be equipped with an agitator, a thermocouple, and a pressure gauge, 3.42 grams (0.0087 mole) of 1,1,1,2,5,5,5-heptafluoro-2-(trifluoromethyl)-4-iodopentane (refer to scheme (2) above) and 0.034 gram ($1.4 \times 10^{-4}$ mole) of dibenzoyl peroxide to form a mixture. The autoclave can then be sealed and heated to about 95° C. whereupon ethylene gas can be delivered to the autoclave to form a reaction mixture so that a pressure of about 350 psig can be achieved. The autoclave pressure can be observed to decline over the course of the reaction and as such the ethylene gas can be continuously delivered to the autoclave so that an autoclave pressure of about 300 psig can be maintained for about one hour. Then the reaction mixture can be degassed and analyzed by gas chromatography to afford the product 1,1,1,2-tetrafluoro-2,4-bis(trifluoromethyl)-6-iodohexane having about 81.3 (wt/wt) percent purity. The product structure can be confirmed by NMR analysis.

In further accordance with scheme (21) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2-tetrafluoro-2,4-bis(trifluoromethyl)-6-iodohexane can be added drop wise to form a mixture. Immediately upon addition of the 1,1,1,2-tetrafluoro-2,4-bis(trifluoromethyl)-6-iodohexane to the mixture, the product 5,6,6,6-tetrafluoro-3,5-bis(trifluoromethyl)hex-1-ene can be observed to collect in the receiver flask. The product can be further purified by distillation and the structure can be confirmed by GC/MS and/or NMR analysis.

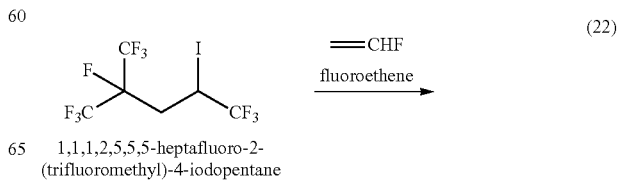

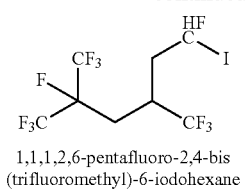

1,1,1,2,6-pentafluoro-2,4-bis(trifluoromethyl)-6-iodohexane

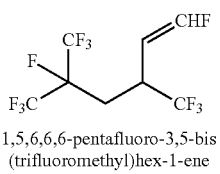

1,5,6,6,6-pentafluoro-3,5-bis(trifluoromethyl)hex-1-ene

Referring to scheme (22) above, in an autoclave that can be equipped with an agitator, a thermocouple, and a pressure gauge, an amount of 1,1,1,2,5,5,5-heptafluoro-2-(trifluoromethyl)-4-iodopentane (refer to scheme (2) above) and catalyst can be added to form a mixture. The autoclave can then be sealed and heated to from about 60° C. to about 195° C. whereupon fluoroethylene gas can be delivered to the autoclave to form a reaction mixture. The fluorethylene gas can be continuously delivered to the autoclave so that an autoclave pressure of about 300 psig can be maintained for from about one hour to about 16 hours. Then the reaction mixture can be degassed and analyzed by gas chromatography to afford the product 1,1,1,2,6-pentafluoro-2,4-bis(trifluoromethyl)-6-iodohexane. The product structure can be confirmed by NMR analysis.

In further accordance with scheme (22) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6-pentafluoro-2,4-bis(trifluoromethyl)-6-iodohexane can be added drop wise to form a mixture. Immediately upon addition of the 1,1,1,2,6-pentafluoro-2,4-bis(trifluoromethyl)-6-iodohexane to the mixture, the product 1,5,6,6,6-pentafluoro-3,5-bis(trifluoromethyl)hex-1-ene can be observed to collect in the receiver flask. The product can be further purified by distillation and the structure can be confirmed by GC/MS and/or NMR analysis.

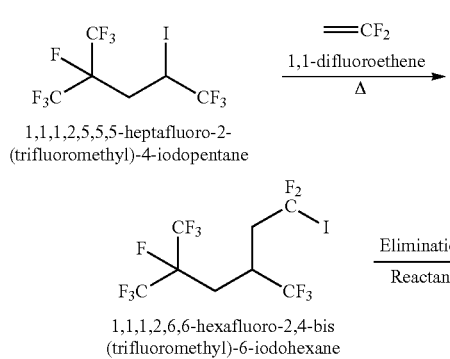

(23)

1,1,1,2,5,5,5-heptafluoro-2-(trifluoromethyl)-4-iodopentane 1,1,1,2,6,6-hexafluoro-2,4-bis(trifluoromethyl)-6-iodohexane

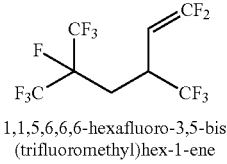

1,1,5,6,6,6-hexafluoro-3,5-bis(trifluoromethyl)hex-1-ene

Referring to scheme (23) above, in an autoclave that can be equipped with an agitator, a thermocouple, and a pressure gauge, an amount of 1,1,1,2,5,5,5-heptafluoro-2-(trifluoromethyl)-4-iodopentane (refer to scheme (2) above) and catalyst can be added to form a mixture. The autoclave can then be sealed and heated to from about 60° C. to about 195° C. whereupon 1,1-difluoroethylene gas can be delivered to the autoclave to form a reaction mixture. The 1,1-difluorethylene gas can be continuously delivered to the autoclave so that an autoclave pressure of about 300 psig can be maintained for from about one hour to about 16 hours. Then the reaction mixture can be degassed and analyzed by gas chromatography to afford the product 1,1,1,2,6,6-hexafluoro-2,4-bis(trifluoromethyl)-6-iodohexane. The product structure can be confirmed by NMR analysis.

In further accordance with scheme (23) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,6-hexafluoro-2,4-bis(trifluoromethyl)-6-iodohexane can be added drop wise to form a mixture. Immediately upon addition of the 1,1,1,2,6,6-hexafluoro-2,4-bis(trifluoromethyl)-6-iodohexane to the mixture, the product 1,1,5,6,6,6-hexafluoro-3,5-bis(trifluoromethyl)hex-1-ene can be observed to collect in the receiver flask. The product can be further purified by distillation and the structure can be confirmed by GC/MS and/or NMR analysis.

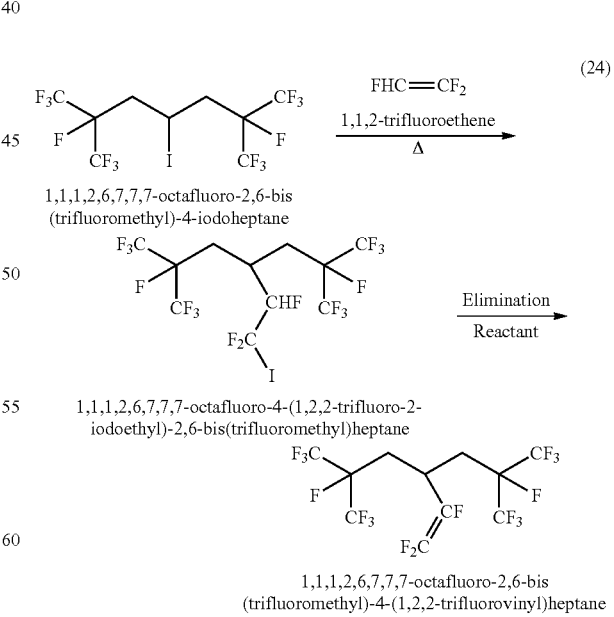

(24)

1,1,1,2,6,7,7,7-octafluoro-2,6-bis(trifluoromethyl)-4-iodoheptane 1,1,1,2,6,7,7,7-octafluoro-4-(1,2,2-trifluoro-2-iodoethyl)-2,6-bis(trifluoromethyl)heptane 1,1,1,2,6,7,7,7-octafluoro-2,6-bis(trifluoromethyl)-4-(1,2,2-trifluorovinyl)heptane According to scheme (24) above, into an autoclave that can be equipped with a dip tube, thermocouple, agitator, pressure gauge, and an attachment to a reservoir containing 1,1,2- trifluoroethylene gas, an amount of 1,1,1,2,6,7,7,7-octafluoro-2,6-bis(trifluoromethyl)-4-iodoheptane (refer to scheme (16) above) and a sufficient amount of catalyst can be added to form a mixture. The autoclave can then be sealed, evacuated, and heated to from about 50° C. to about 120° C. 1,1,2-trifluoroethylene gas can be added to the mixture to form a reaction mixture. The reaction mixture can be held at a sufficient pressure for from about four hours to about 16 hours. The reaction mixture can then be chilled using an ice water bath and degassed to provide 1,1,1,2,6,7,7,7-octafluoro-4-(1,2,2-trifluoro-2-iodoethyl)-2,6-bis(trifluoromethyl)heptane product. The product can be purified by vacuum distillation and the structure confirmed by NMR analysis.

In further accordance with scheme (24) above, in a flask that can be equipped with an agitator, thermocouple, addition funnel, and Vigreux column with a Claisen side arm equipped with a reflux condenser, thermocouple, and a receiver flask, a sufficient amount of an elimination reactant can be placed and heated to from about 25° C. to about 100° C. To the elimination reactant, a sufficient amount of 1,1,1,2,6,7,7,7-octafluoro-4-(1,2,2-trifluoro-2-iodoethyl)-2,6-bis(trifluoromethyl)heptane can be added drop wise to form a mixture. Immediately upon addition of the 1,1,1,2,6,7,7,7-octafluoro-4-(1,2,2-trifluoro-2-iodoethyl)-2,6-bis(trifluoromethyl)heptane, to the mixture, the product 1,1,1,2,6,7,7,7-octafluoro-2,6-bis(trifluoromethyl)-4-(1,2,2-trifluorovinyl)heptane can be observed to collect in the receiver flask. The product can be further purified by distillation and the structure can be confirmed by GC/MS and/or NMR analysis.

(25)

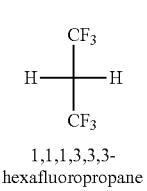
1,1,1,3,3,3-
hexafluoropropane

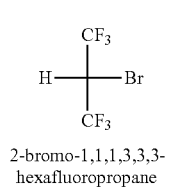
2-bromo-1,1,1,3,3,3-
hexafluoropropane

+

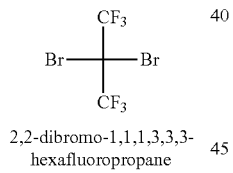
2,2-dibromo-1,1,1,3,3,3-
hexafluoropropane

According to scheme (25) above, to a 100 cc three-neck flask that can be equipped with a thermometer, a Teflon dip tube that can be connected to a supply of 1,1,1,3,3,3-hexafluoropropane, and an outlet tube that can be connected to a ½"×12" stainless steel tube reactor, liquid bromine can be placed. The flask can be warmed by an electric heating lamp to produce a vapor temperature of from about 35° C. to about 40° C. The tube reactor can be heated to from about 540° C. to about 550° C. by an electric furnace. To the flask, 28 mL/min of 1,1,1,3,3,3-hexafluoropropane gas measured by a flow meter can be bubbled through the bromine liquid via the dip tube and consequently saturated with the bromine vapor to produce a mixture. The mixture can be carried to the tube reactor via the outlet tube. As the mixture passes through the tube reactor the reaction takes place and the 2-bromo-1,1,1,3,3,3-hexafluoropropane product can be collected in an ice/water trap, washed with water and analyzed by gas chromatography, to afford the following product distribution 63 (wt/wt)% 1,1,1,3,3,3-hexafluoropropane, 34 (wt/wt)% 2-bromo-1,1,1,3,3,3-hexafluoropropane and 1.9 (wt/wt)% 2,2-dibromo-1,1,1,3,3,3-hexafluoropropane. The product can be isolated by distillation. The product structure(s) can be confirmed by GC/MS and/or NMR analysis.

Exemplary $R_F$-intermediates as well as $R_F$-olefin products can be prepared according to schemes 26 through 30 below following the general procedures described herein.

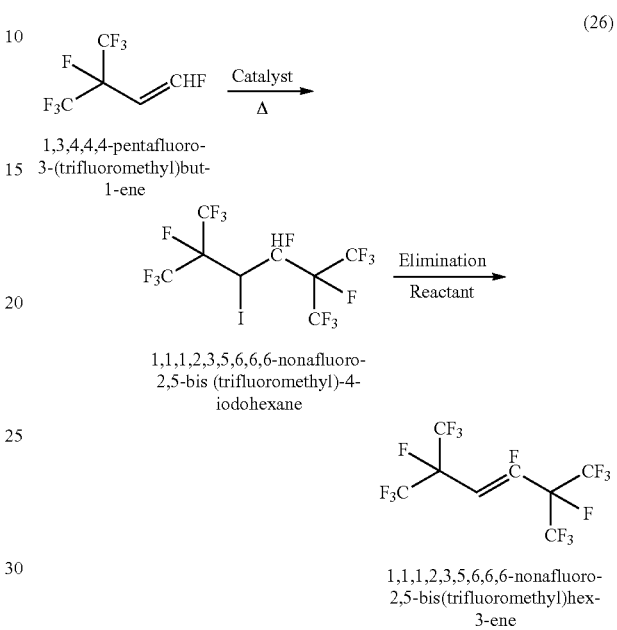

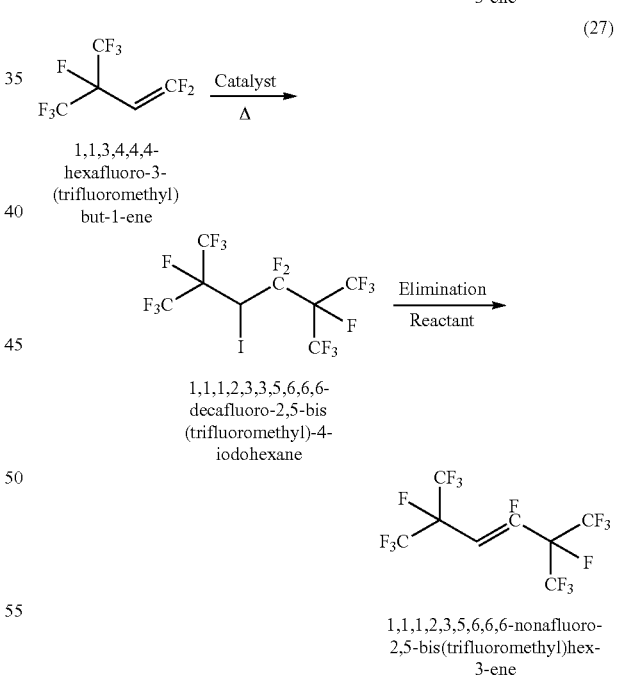

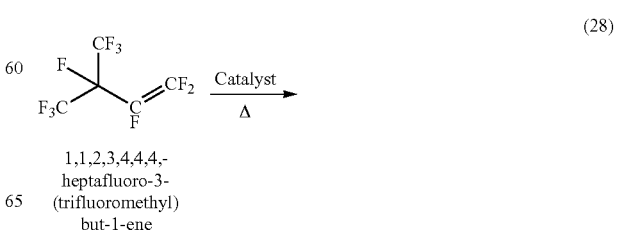

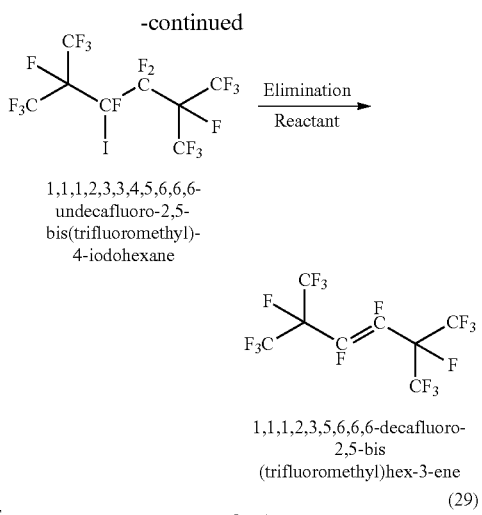

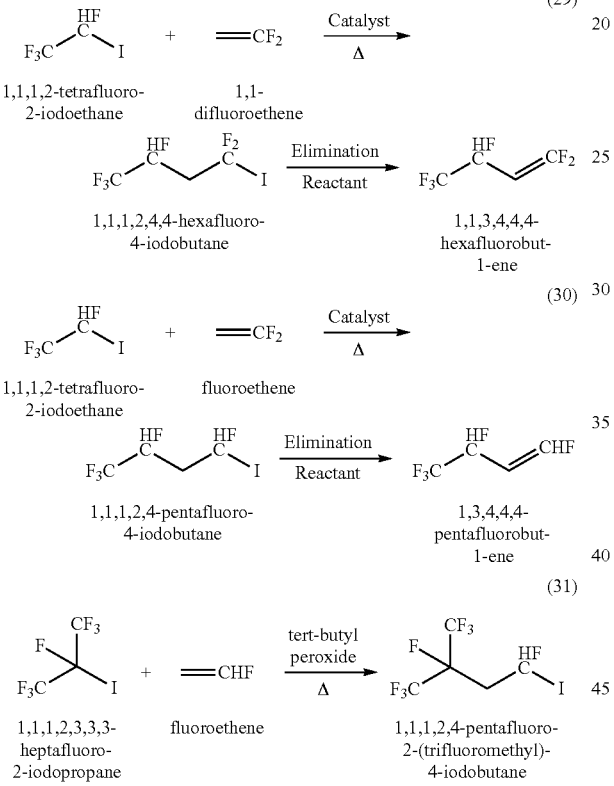

According to scheme (31) above, in a 2 L Parr reactor (316 stainless steel) that can be equipped with a rupture disc, pressure gauge, dip tube with valve, vapor valve, cooling loop, and a thermowell, 1189 grams (4.02 moles) of 1,1,1,2,3,3,3-heptafluoro-2-iodopropane and 13 grams (0.09 mole) of tert-butyl peroxide can be placed to form a mixture. The reactor can be sealed and heated to about 120° C. while stirring. An autogenous reactor pressure can be observed to be about 100 psig. To the mixture, vinyl fluoride (fluoroethene, VF) can be added to achieve and/or maintain a reactor pressure of about 200 psig to form a reaction mixture. An exotherm can be observed along with a reactor pressure drop while the temperature remained below about 150° C. The reaction can be continued until the reactor pressure stabilizes. The reactor can be vented and the contents removed to afford about 1387 grams of the crude 1,1,1,2,4-pentafluoro-2-(trifluoromethyl)-4-iodobutane containing product mixture. The product mixture can be analyzed by gas chromatography to afford 2.6% VF, 0.8% CH3I, 84.6% 1,1,1,2,4-pentafluoro-2-(trifluoromethyl)-4-iodobutane, 0.7% peroxide, 8.3% 1,1,1,2,4,6-hexafluoro-2-(trifluoromethyl)-6-iodohexane (not shown), and 3.0% other. Telomers, in addition to those described above, can be formed (e.g., 1,1,1,2,4,6,8-heptafluoro-2-(trifluoromethyl)-8-iodooctane, 1,1,1,2,4,6,8,10-octafluoro-2-(trifluoromethyl)-10-iodododecane, etc.). The product mixture can be distilled in a 1 L flask equipped with an agitator, thermometer, and a silver-lined, vacuum jacketed column. The column can be 19.5" long with a packed length of 13.5" and packed with 0.16" Monel™ (Inco Limited 145 King Street West Suite 1500 Toronto, Ontario M5H 4B7, Canada) Pro-Pak® (Cannon Instrument Company, 2139 High Tech Rd., State College, Pa. 16803). The column can be equipped with a magnetic take-off head with thermometer, condenser, and receiver flask. The distillation can afford about 1205 grams of 98.5% to 99.0% (by gas chromatography) of the 1,1,1,2,4-pentafluoro-2-(trifluoromethyl)-4-iodobutane product. The product structure can be confirmed by NMR and/or chromatographic and/or spectroscopic analysis.

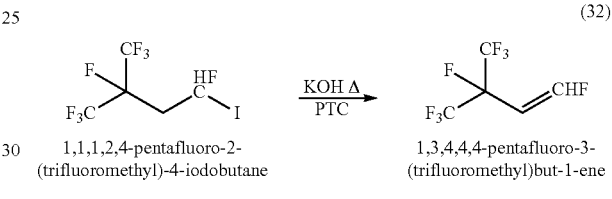

In accordance with scheme (32) above, in a 2 L flask that can be equipped with an agitator, thermometer, addition funnel for the addition of 1,1,1,2,4-pentafluoro-2-(trifluoromethyl)-4-iodobutane (refer to scheme (31) above), and a Claisen distillation head side-arm that can be equipped with a condenser at about 0° C. along with an adapter that can be equipped with a cold trap and a chilled receiver flask, 238 grams (4.24 moles) of potassium hydroxide (KOH), 670.4 grams of water and 30 grams of a 75% (wt/wt) solution of methyltributylammonium chloride in water (aliquat 175) can be placed to form a mixture. The mixture can be heated to from about 75° C. to about 80° C. To the heated mixture, 893 grams of 1,1,1,2,4-pentafluoro-2-(trifluoromethyl)-4-iodobutane can be drop wise added to form a reaction mixture. From the reaction mixture, 405 grams of 1,3,4,4,4-pentafluoro-3-(trifluoromethyl)but-1-ene can be collected from the receiver flask.

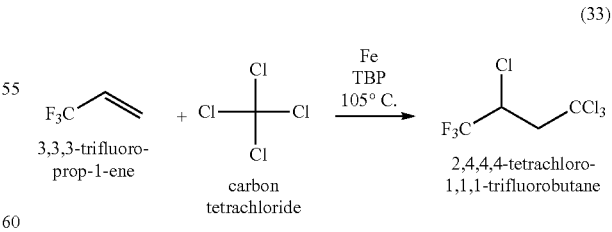

Referring to scheme (33) above, in a 600 mL autoclave that can be equipped with an agitator, thermocouple, relief valves, sample valves and a pressure gauge, about 200 mL carbon tetrachloride, 6 gram (0.11 mole) of iron powder and 6 grams (0.023 mole) of tributyl phosphate (TBP) can be added to form a mixture. The reactor can be cooled down to about −50°

C. by placing the autoclave in a dry ice/acetone bath, a vacuum can be pulled. To the mixture, 3,3,3-trifluoroprop-1-ene can be added to develop an internal pressure of about 3.4 kPa to for a reaction mixture. The reaction mixture can be heated to about 105° C. thereby producing an autogenous pressure of about 7.7 kPa. The reaction mixture can be maintained at temperature for several hours during which time the reactor pressure can be observed to decrease and settle at 2.4 kPa. To the reaction mixture, additional 3,3,3-trifluoroprop-1-ene can be fed discretely several times to drive the reaction to completion. The reaction can be observed to be complete when the absence of a pressure decrease is evident. The contents of the autoclave can transferred and distilled to afford the 2,4,4,4-tetrachloro-1,1,1-trifluoro-butane product that can have a boiling point of 86° C. at 163 mmHg. The product structure can be confirmed by NMR and/or GCMS analysis.

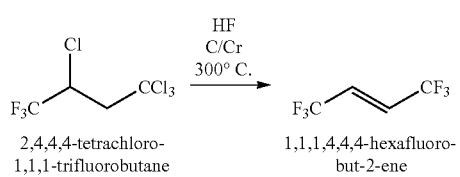

(34)

2,4,4,4-tetrachloro-1,1,1-trifluorobutane → 1,1,1-4,4,4-hexafluoro-but-2-ene

Referring to scheme (34) above, to a reactor that can have an outside diameter of about 19 mm and a length of about by 600 mm and can be composed of an Inconel® alloy, equipped with a heater, thermocouple, product trap, and a syringe pump, a chromium comprising carbon catalyst can be added to form a reactor space. The reactor space can be heated to from about 250° C. to about 350° C. and exposed to $N_2$ and a $HF/N_2$ mixture for about 16 hours. The reactor space can be cooled and maintained at about 300° C. and about 270 mL/minute of gaseous HF and about 11.4 mL/hour of liquid 2,4,4,4-tetrachloro-1,1,1-trifluorobutane (refer to scheme (33) above) can be delivered through the syringe pump and into a pre-heater to vaporize the 2,4,4,4-tetrachloro-1,1,1-trifluorobutane to form a reaction mixture. The reaction mixture can be washed with water, dried over $MgSO_4$ and collected in a dry-ice condenser to afford the crude 1,1,1-4,4,4-hexafluoro-2-butene product. Distillation of the crude product yielded 99% pure product that can have a boiling point of about 8° C. The product structure can be confirmed by NMR and/or GCMS analysis.

The present disclosure also provides combustion prevention compositions which can include the $R_F$-olefin products described herein, for example, that can prevent as well as extinguish combustion through inerting and/or dilution, as well as chemical, physical and/or thermal extinguishment and/or prevention methods. Thermal extinguishing includes "cooling" a combustion. The present disclosure also provides methods of extinguishing, preventing, and/or suppressing combustion using such compounds.

The combustion prevention composition can include

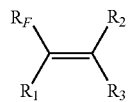

with; $R_F$ being a fluorine containing moiety including $(CF_3)_2$ $CFCH_2(CF_3)CH-$, $(CF_3)_2CFCH_2((CF_3)_2CF)CH-$, $(CF_3)_2$ $CFCH_2((CF_3)_2CH)CH-$, $(CF_3)_2CHCH_2((CF_3)_2CF)CH-$, $((CF_3)_2CFCH_2)_2CH-$, $(CF_3)_2CFCH_2CF-$, $(CF_3)_2CF-$, $(CF_3)_2CH-$, $CF_3-$, or $C_nF_{2n+1}-$, n being an integer from 2 to 20; $R_1$ being F or H; $R_2$ including $(CF_3)_2CF-$, $(CF_3)_2CH-$, $CF_3-$, F, or H; and $R_3$ including $(CF_3)_2CF-$, $(CF_3)_2CH-$, $CF_3-$, F, or H. The combustion prevention composition can also include

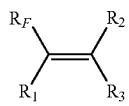

with $R_F$ being a fluorine containing moiety comprising $(CF_3)_2$ $CFCH_2(CF_3)CH-$, $(CF_3)_2CFCH_2((CF_3)_2CF)CH-$, $(CF_3)_2$ $CFCH_2((CF_3)_2CH)CH-$, $(CF_3)_2CHCH_2((CF_3)_2CF)$ $CH-$, $((CF_3)_2CFCH_2)_2CH-$, $(CF_3)_2CFCH_2CF-$, $(CF_3)_2$ $CF-$, $(CF_3)_2CH-$, $CF_3-$, or $C_nF_{2n+1}-$, n being an integer from 2 to 20, $R_1$ being F or H, $R_2$ being $(CF_3)_2CF-$, $(CF_3)_2$ $CH-$, $CF_3-$, F, or H, and $R_3$ being $(CF_3)_2CF-$, $(CF_3)_2$ $CH-$, $CF_3-$, F, or H.

The combustion prevention compositions can also include $R_F-CR_1=CR_2R_3$, with the $R_F$ portion being $C_3F_7$ or $C_3F_6$, and the $R_1$, $R_2$, and $R_3$ portions being one or more of H, F, $CF_3$, and $C_3F_7$. $R_F-CR_1=CR_2R_3$ can be

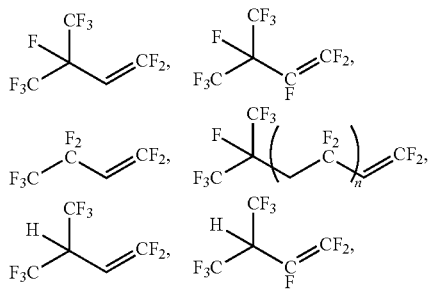

The present disclosure further provides combustion prevention, fire extinguishing, preventing, and/or suppressing systems for delivering such fire extinguishing agents. Exemplary aspects of the present disclosure are described with reference to FIG. 3. Referring to FIG. 3, space 37 configured with a fire extinguishing system 38 is shown. System 38 includes an extinguishing agent storage vessel or container 40 contiguous with a composition distribution apparatus 42 such as an extinguishing agent dispersing nozzle.

The apparatus can be configured to distribute the combustion prevention composition within space 37. The apparatus can also be configured to provide the composition to the space automatically upon the detection of combustion within the space. The distribution apparatus can be configured to distribute the composition in substantially liquid form and/or gaseous form. The distribution apparatus can be a streaming apparatus that may be configured to distribute the composition in a substantially liquid form. The distribution apparatus may be configured to distribute the composition in substantially gaseous form, such as from a flooding apparatus.

As depicted, a combustion 44 occurs within a pan 46 on a pedestal 48. An extinguishing mixture 50 exists within space 37 as applied to the combustion to substantially extinguish the flame.

While depicted in two dimensions, space 37, for purposes of this disclosure, should be considered to have a volume determined from its dimensions (e.g. width, height, and length). While FIG. 3 illustrates a system configured for preventing combustion within a space, as illustrated, it appears to be enclosed, the application of the mixtures, systems, and/or methods of the present disclosure are not so limited. In some aspects, the present disclosure may be used to extinguish and/or prevent combustion in open spaces, as well as, confined spaces. All combustion suitable for extinguishment, suppression, and/or prevention using the mixtures of the present disclosure are at least partially surrounded by a space. The available volume of this space can be filled with agents of the present disclosure to extinguish, suppress, and/or prevent combustion. Typically, the available volume is that volume which can be occupied by a liquid or gas (i.e. that volume which fluids (gases and liquids) can exchange). Solid constructions typically are not part of the available volume.

Furthermore, FIG. 3 illustrates a single container 40. It should be understood that the combustion prevention composition can be provided to space 37 from multiple containers and the present disclosure should not be limited to mixtures, methods, and/or systems that can be provided from a single vessel nor methods or systems that utilize a single vessel. Generally, the combustion is extinguished when the extinguishing mixture is introduced from the vessel through nozzle 42 to the space. It should also be understood that while FIG. 3 illustrates a single nozzle as the distribution apparatus, multiple nozzles may be utilized and the present disclosure should not be limited to mixtures, methods, and/or systems utilizing a single nozzle.

According to an aspect of the disclosure, the combustion prevention composition can comprise, consist essentially of, and/or consist of the $R_F$-olefin product described above such as

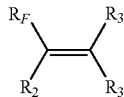

including those $R_F$-compositions in Table 3 below. The combustion prevention composition can include

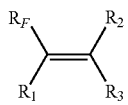

with $R_F$ being a fluorine containing moiety such as $(CF_3)_2CFCH_2(CF_3)CH$—, $(CF_3)_2CFCH_2((CF_3)_2CF)CH$—, $(CF_3)_2CFCH_2((CF_3)_2CH)CH$—, $(CF_3)_2CHCH_2((CF_3)_2CF)CH$—, $((CF_3)_2CFCH_2)_2CH$—, $(CF_3)_2CFCH_2CF$—, $(CF_3)_2CF$—, $(CF_3)_2CH$—, $CF_3$—, or $C_nF_{2n+1}$—, n being an integer from 2 to 20, $R_1$ is F or H; $R_2$ including $(CF_3)_2CF$—, $(CF_3)_2CH$—, $CF_3$—, F, or H; and $R_3$ including $(CF_3)_2CF$—, $(CF_3)_2CH$—, $CF_3$—, F, or H.

TABLE 3

Exemplary $R_F$-Compositions

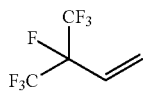
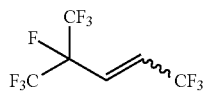

TABLE 3-continued

Exemplary $R_F$-Compositions

The combustion prevention composition can also comprise, consist essentially of, and/or consist of the $R_F$-composition and a suppressing additive and/or other fire extinguishing agents. The suppressing additive employed can include gases, water, and/or mixtures thereof. Exemplary gases can include nitrogen, argon, helium, carbon dioxide, and/or mixtures thereof. In an exemplary aspect, these gases can deprive fires of necessary fuels, such as oxygen. In the same or other aspects, these gases resist decomposition when exposed to combustion. In some cases, these gases are referred to as inert gases and/or propellants. An exemplary inert gas can comprise, consist essentially of, and/or consist of nitrogen. The composition distribution apparatus 38 may be configured to force the composition from the container and through a nozzle using a propellant, such as nitrogen and/or a hydrofluorocarbon.

The extinguishing mixture can include those compounds described above with reference to Table 2, and as such, they include those compounds such as $R_F(R_2)C=C(R_3)_2$. These compounds may be used alone or as admixtures with each other or as blends with other fire extinguishing agents. The agents of this invention are suitable for use in both total flooding and portable fire suppression applications. Suitable extinguishing agents for blends with the $R_F$-olefin products include $CF_3CHFCF_3$, $CF_3CF_2CF_2H$, $CF_3CH_2CF_3$, $CF_3CHFCF_2H$, $CF_3CF_2H$, and/or $CF_3H$. The olefin product, as well as, admixtures, and/or blends can be applied to space 37 at certain volume to volume percentages. It should be understood that in the % (v/v) values set forth in this description are based in space volume and refer to design concentration as adopted and described by the National Fire Protection Association in NFPA 2001 standard on clean agent fire extinguishing, 2000 edition. The equation used to calculate the concentration of extinguishing compounds has likewise been adopted by the National Fire Protection Association and is as follows:

$$W = V/S(C/100 - C)$$

Where:
W=weight of extinguishing compound (kg)
V=volume of test space (m$^3$)
S=a specific volume of extinguishing compound at test temperature (m$^3$\kg)
C=concentration (% (v\v)).

In particular aspects an extinguishing mixture comprising, consisting essentially of, and/or consisting of the compounds listed in Table 2 may be employed at concentrations of about 6%, and/or less than 6%, for example, as represented in Table 4 below.

TABLE 4

Cup Burner Results for Extinguishment of Heptane*

| R$_F$-Composition | Agent in Space % (v/v) |
|---|---|
| 3,4,4,4-tetrafluoro-3-(trifluoromethyl)but-1-ene | 5.5 |
| 1,1,1,4,5,5,5-heptafluoro-4-(trifluoromethyl)pent-2-ene | 5.4 |
| 1,1,1,2,3,4,5,5-nonafluoro-4-(trifluoromethyl)pent-2-ene | 5.2 |
| 1,3,4,4,4-pentafluoro-3-(trifluoromethyl)but-1-ene | 5.3 |
| 1,1,3,4,4,4-hexafluoro-3-(trifluoromethyl)but-1-ene | 4.9 |
| 1,1,1-4,4,4-hexafluoro-2-butene | 5.9 |

*Data obtained according to ISO 14520-1:2000/Cor 1:2002

R$_F$-compositions may be applied using conventional application techniques and methods used for Halon such as Halon 1301 and Halon 1211. Thus, these compositions may be used in total flooding combustion prevention system in which the composition is introduced to an enclosed region (e.g. a room or other enclosure) surrounding a fire in a concentration sufficient to extinguish the fire. In accordance with the present disclosure, a total flooding system apparatus, equipment, or even rooms of an enclosure may be provided with a source of an composition and appropriate piping valves and controls as to automatically and/or manually introduce an appropriate concentration in the event that a combustion should occur. Thus, the combustion prevention composition may be pressurized with nitrogen or other inert gas up to about 600 psig at ambient conditions. Alternatively, the compositions may be applied to combustion through the use of conventional portable fire extinguishing equipment.

Systems containing the olefinic agent, in accordance with this disclosure, may be conveniently pressurized at any desirable pressure up to about 600 psig at ambient conditions. Some of the applications of the olefinic agents of this disclosure are the extinguishing of liquid and gaseous fueled fires, the protection of electrical equipment, ordinary combustibles such as wood, paper, and/or textiles, hazardous solids, and the protection of computer facilities, data processing equipment, and control rooms. The novel agents according to the present disclosure can also be introduced to a fire for suppression purposes as a liquid or gas or a combination of both. This is sometimes referred to as utilizing a composition as a streaming agent. The novel compounds according to the present invention can be introduced to fires in combination with other compounds as blends.

The invention claimed is:

1. A fire extinguishing agent comprising a propellant 1,3,4,4,4-pentafluoro-3-(trifluoromethyl)but-1-ene.

2. The fire extinguishing agent of claim 1, wherein the propellant is nitrogen.

3. The fire extinguishing agent of claim 1, wherein the propellant is a hydrofluorocarbon.

4. A combustion prevention system comprising:
 a container housing
 a combustion prevention composition, comprising
  a propellant and the fire extinguishing agent of claim 1 and
  a composition distribution apparatus coupled to the container, the apparatus configured to distribute the combustion prevention composition.

5. The system of claim 4 wherein the system is configured as a total flooding system.

* * * * *